(12) United States Patent
Kawano et al.

(10) Patent No.: US 11,988,636 B2
(45) Date of Patent: May 21, 2024

(54) METHOD FOR PARTICLE ANALYSIS AND METHOD FOR PARTICLE PRODUCTION

(71) Applicants: KAWANO Lab. Inc., Osaka (JP); TableMark Co., Ltd., Tokyo (JP)

(72) Inventors: Makoto Kawano, Ikeda (JP); Ayako Tatematsu, Tokyo (JP); Ryosuke Abe, Tokyo (JP)

(73) Assignees: KAWANO Lab. Inc., Osaka (JP); TableMark Co., Ltd., Tokyo (JP)

( * ) Notice: Subject to any disclaimer, the term of this patent is extended or adjusted under 35 U.S.C. 154(b) by 985 days.

(21) Appl. No.: 16/858,432

(22) Filed: Apr. 24, 2020

(65) Prior Publication Data

US 2020/0340947 A1     Oct. 29, 2020

(51) Int. Cl.
*G01N 27/76* (2006.01)
*A23L 27/00* (2016.01)
(Continued)

(52) U.S. Cl.
CPC .............. *G01N 27/76* (2013.01); *A23L 27/72* (2016.08); *A23P 10/30* (2016.08);
(Continued)

(58) Field of Classification Search
CPC .......... G01N 27/76; G01N 2015/1075; G01N 2015/1493; G01N 33/56961; G01N 30/86;
(Continued)

(56) References Cited

U.S. PATENT DOCUMENTS 7,439,743 B2 * 10/2008 Potter ...................... G01V 3/26
324/201
10,656,119 B2    5/2020 Kawano
(Continued)

FOREIGN PATENT DOCUMENTS

JP       H07-289885 A      11/1995
JP       H08-243378 A       9/1996
(Continued)

OTHER PUBLICATIONS

Lee, Hojae, et al. "Turning diamagnetic microbes into multinary micro-magnets: magnetophoresis and spatio-temporal manipulation of individual living cells." Scientific Reports 6.1 (2016): 38517. (Year: 2016).*

(Continued)

*Primary Examiner* — Christopher P McAndrew
(74) *Attorney, Agent, or Firm* — Studebaker & Brackett PC

(57) ABSTRACT

The method for particle analysis includes a first magnetic susceptibility measurement step S4 of measuring a volume magnetic susceptibility of each of first particles p1; an encapsulation treatment step S5 of performing an encapsulation treatment so that the first particles p1 encapsulate an encapsulation target component pt smaller than the first particles p1; a second magnetic susceptibility measurement step S8 of measuring a volume magnetic susceptibility of each of second particles p2 as an analysis target that are the first particles p1 after the encapsulation treatment; and a step S9 of analyzing whether or not the encapsulation target component pt is encapsulated in the second particles p2 based on a result of measurement in the first magnetic susceptibility measurement step S4 and a result of measurement in the second magnetic susceptibility measurement step S8.

6 Claims, 10 Drawing Sheets

(51) Int. Cl.
*A23P 10/30* (2016.01)
*B01J 13/02* (2006.01)
*G01N 15/00* (2006.01)
*G01N 15/10* (2006.01)
*G01N 15/1031* (2024.01)
*B01J 13/04* (2006.01)

(52) U.S. Cl.
CPC ........... *G01N 15/1031* (2013.01); *B01J 13/02* (2013.01); *B01J 13/04* (2013.01); *G01N 2015/0038* (2013.01); *G01N 2015/1027* (2024.01)

(58) Field of Classification Search
CPC ............... G01N 15/1459; G01N 30/88; G01N 2015/1087; G01N 15/1031; G01N 2015/0053; G01N 2333/39; G01N 2015/0065; G01N 33/5432; G01N 15/0227; G01N 33/54326; G01N 2015/0038; A23L 27/07; A23P 10/30; B01J 13/02; B01J 13/04
USPC .......................................................... 324/201
See application file for complete search history.

(56) References Cited

U.S. PATENT DOCUMENTS

| | | |
|---|---|---|
| 10,739,240 B2 | 8/2020 | Kawano |
| 2005/0118273 A1 | 6/2005 | Sasaki et al. |
| 2013/0285648 A1* | 10/2013 | Kim .................... G01R 33/1238 324/201 |
| 2018/0196004 A1 | 7/2018 | Kawano |
| 2018/0313738 A1 | 11/2018 | Kawano |

FOREIGN PATENT DOCUMENTS

| | | |
|---|---|---|
| WO | 2003/041509 A1 | 5/2003 |
| WO | 2016/208724 A1 | 12/2016 |
| WO | 2017/069260 A1 | 4/2017 |
| WO | 2019/039601 A1 | 2/2019 |

OTHER PUBLICATIONS

Tatematsu et al., Film Permeability Control Using Yeast Capsule and Evaluation Thereof, announced in lecture proceedings (Web ver.), issued May 4, 2019, used in the discussion meeting on the 79th conference of the Japan Society for Analytical Chemistry, Kitakyushu International Conference Center and AIM, May 18-19, 2019.
Tatematsu et al., Role of Cell Wall Interface in Yeast Capsule Inclusion and Evaluation Thereof, announced in lecture proceedings (Web ver.), issued Aug. 28, 2019, used in the discussion meeting on the 68th conference of the Japan Society for Analytical Chemistry, held in Nishi-Chiba campus of Chiba University, Sep. 11, 2019.
An Office Action; "Notice of Reasons for Refusal," mailed by the Japanese Patent Office on Apr. 2, 2024, which corresponds to Japanese Patent Application No. 2020-071695 and is related to U.S. Appl. No. 16/858,432; with English language translation.
Mori Sayaka et al., "Evaluation of Yeast Cells Using Magnetic Susceptibility", 77th Symposium of Analytical Chemistry, Japan Society for Analytical Chemistry, May 27-28, 2017, p. 146, P2040.

* cited by examiner

METHOD FOR PARTICLE ANALYSIS AND METHOD FOR PARTICLE PRODUCTION

INCORPORATION BY REFERENCE

The present application claims priority under 35 U.S.C. § 119 to Japanese Patent Application No. 2019-86365, filed on Apr. 26, 2019 and Japanese Patent Application No. 2020-71695, filed on Apr. 13, 2020. The contents of the applications are incorporated herein by reference in their entirety.

BACKGROUND

The present disclosure relates to a method for analyzing particles encapsulating an encapsulation target component such as microcapsules, and a method for producing particles encapsulating an encapsulation target component such as microcapsules.

Microcapsules are particles encapsulating a liquid or solid component. Microcapsules each have a particle diameter less than 1 mm. Microcapsules have a coating (capsule substrate) covering the encapsulated component. For example, various techniques have been proposed for industrially producing microcapsules each encapsulating an active component, such as a pharmaceutical, an agricultural chemical, a fragrance, or a food material. Methods for producing a microcapsule include, for example, a chemical technique, a physical technique, and a biological technique. Examples of the chemical technique include interfacial polymerization, a coating-film method by curing in a liquid, and molecular inclusion using cyclodextrin. Examples of the physical technique include spray drying, spray cooling, and air suspension coating. Examples of the biological technique include a method in which a component is encapsulated in a cell envelope of yeast or the like.

Biological techniques mainly use a yeast-derived capsule substrate. A yeast-derived capsule substrate is composed of a cell envelope of yeast remaining after removal of soluble contents from yeast. A cell envelope contains a cell wall, a cell membrane, and other solid components. Specifically, the yeast-derived capsule substrate is composed of solid components of yeast remaining after removal of intracellular soluble components from yeast by a washing treatment, an enzyme treatment, or the like. A cell envelope such as a cell wall of yeast is used as a capsule substrate. For example, Japanese Unexamined Patent Application Publication No. 8-243378 discloses a technique in which yeast is treated with an enzyme to release intracellular components outside the cells.

Japanese Unexamined Patent Application Publication No. 8-243378 discloses encapsulating a hydrophobic substance or a hydrophilic substance in a yeast-derived capsule substrate. Japanese Unexamined Patent Application Publication No. 8-243378 discloses that the hydrophobic substance is at least one derived lipid selected from the group consisting of long-chain hydrocarbons, long-chain alcohols, long-chain amino alcohols, long-chain aldehydes, long-chain ketones, long-chain acids and salts thereof, terpenoids, steroids, and carotenoids. Japanese Unexamined Patent Application Publication No. 8-243378 also discloses that the hydrophilic substance is at least one substance selected from the group consisting of amino acids, water-soluble vitamins, nucleotides, and sugars.

In addition, Japanese Unexamined Patent Application Publication No. 8-243378 discloses that the yeast is at least one type of microorganism selected from the group consisting of *Saccharomyces cerevisiae*, *Saccharomyces rouxii*, *Saccharomyces curlsbergensisi*, *Candida utilis*, *Candida tropicalis*, *Candida lipolytica*, and *Candida flaveri*.

In order to quantitatively analyze whether or not an encapsulation target component is encapsulated in microcapsules, a high performance liquid chromatograph (HPLC) is generally used, for example. Specifically, an encapsulated component is extracted from microcapsules and quantified using a high performance liquid chromatograph. Based on the measurement result, an amount of the encapsulated component per gram of the microcapsules is calculated to analyze (evaluate) whether or not the encapsulation target component is encapsulated in the microcapsules. However, the quantitative analysis using a high-performance liquid chromatograph can provide only estimation on whether or not an encapsulation target component is encapsulated in microcapsules (analysis target particles).

SUMMARY

The method for particle analysis according to an aspect of the present disclosure includes a first observation step of observing first particles subjected to magnetophoresis, a first migration velocity measurement step of measuring a magnetophoretic velocity of the first particles based on an observation result in the first observation step; a first magnetic susceptibility measurement step of measuring a volume magnetic susceptibility of each of the first particles based on a result of measurement in the first migration velocity measurement step; an encapsulation treatment step of performing an encapsulation treatment so that the first particles encapsulate an encapsulation target component smaller than the first particles; a second observation step of observing second particles that are the first particles after the encapsulation treatment subjected to magnetophoresis; a second migration velocity measurement step of measuring a magnetophoretic velocity of the second particles based on an observation result in the second observation step; a second magnetic susceptibility measurement step of measuring a volume magnetic susceptibility of each of the second particles based on a result of measurement in the second migration velocity measurement step; and a step of analyzing whether or not the encapsulation target component is encapsulated in the second particles based on a result of measurement in the first magnetic susceptibility measurement step and a result of measurement in the second magnetic susceptibility measurement step.

In an embodiment, the method for particle analysis further includes a step of spectroscopically observing the second particles to analyze whether or not the encapsulation target component is encapsulated in the second particles.

In an embodiment, the method for particle analysis further includes a first zeta potential measurement step of measuring a zeta potential of the first particles; a second zeta potential measurement step of measuring a zeta potential of the second particles; and a step of analyzing whether or not the encapsulation target component is encapsulated in the second particles based on a result of measurement in the first zeta potential measurement step and a result of measurement in the second zeta potential measurement step.

The method for particle production according to an aspect of the present disclosure includes a first observation step of observing first particles subjected to magnetophoresis, a first migration velocity measurement step of measuring a magnetophoretic velocity of the first particles based on an observation result in the first observation step; a first magnetic susceptibility measurement step of measuring a volume magnetic susceptibility of each of the first particles based on a result of measurement in the first migration velocity measurement step; an encapsulation treatment step of performing an encapsulation treatment so that the first particles encapsulate an encapsulation target component smaller than the first particles; a second observation step of observing second particles that are the first particles after the encapsulation treatment subjected to magnetophoresis; a second migration velocity measurement step of measuring a magnetophoretic velocity of the second particles based on an observation result in the second observation step; a second magnetic susceptibility measurement step of measuring a volume magnetic susceptibility of each of the second particles based on a result of measurement in the second migration velocity measurement step; and a step of analyzing whether or not the encapsulation target component is encapsulated in the second particles based on a result of measurement in the first magnetic susceptibility measurement step and a result of measurement in the second magnetic susceptibility measurement step.

In an embodiment, the first particles include the solid components of yeast remaining after release of intracellular components from yeast.

In an embodiment, the method for particle production further includes a first particle production step of producing the first particles. The first particle production step includes a step of causing the yeast to release the intracellular components.

In an embodiment, the encapsulation treatment step includes a step of mixing the first particles and the encapsulation target component in a solvent.

DETAILED DESCRIPTION

Figure 1:
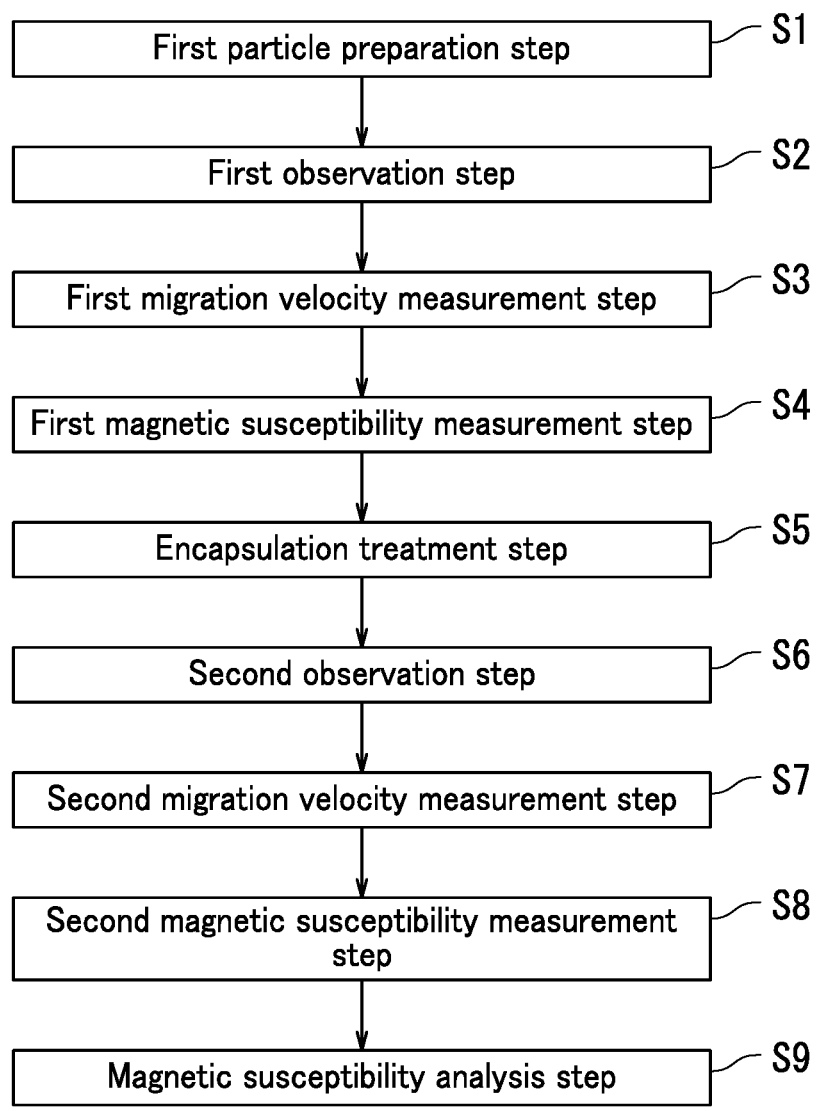
FIG. 1 is a flowchart illustrating a method for particle production according to a first embodiment of the present disclosure.

The following describes embodiments of the present disclosure with reference to drawings. However, the present disclosure is not limited to the following embodiments. Some overlapping explanations may be omitted as appropriate. Note that elements that are the same or equivalent are indicated by the same reference signs in the drawings and description thereof is not repeated.

First Embodiment

With reference to FIG. 1, a method for particle analysis and a method for particle production according to the present embodiment will be described. FIG. 1 is a flowchart illustrating a method for particle production according to the present embodiment. As illustrated in FIG. 1, the method for particle production according to the present embodiment includes a first particle preparation step S1, a first observation step S2, a first migration velocity measurement step S3, a first magnetic susceptibility measurement step S4, an encapsulation treatment step S5, a second observation step S6, a second migration velocity measurement step S7, a second magnetic susceptibility measurement step S8, and a magnetic susceptibility analysis step S9. Among these steps S1 to S9, the first observation step S2, the first migration velocity measurement step S3, the first magnetic susceptibility measurement step S4, the encapsulation treatment step S5, the second observation step S6, the second migration velocity measurement step S7, the second magnetic susceptibility measurement step S8, and the magnetic susceptibility analysis step S9 correspond to the method for particle analysis according to the present embodiment.

<First Particle Preparation Step S1>

In the first particle preparation step S1, first particles p1 are prepared. The first particles p1 have a particle diameter of, for example, 1 nm or more and several hundred μm or less. The first particles p1 are, for example, substrates for microcapsules (capsule substrates). A capsule substrate has a membrane component that separates the outside and the inside thereof. However, the first particles p1 are not limited to capsule substrates. The first particles p1 may be any particles capable of encapsulating an encapsulation target component pt.

The first particles p1 may be, for example, capsule substrates derived from yeast. For example, the capsule substrates derived from yeast are composed of solid components of yeast remaining after release of intracellular components from yeast. In this case, the capsule substrates derived from yeast are mainly composed of cell envelope of yeast. Specifically, the capsule substrates derived from yeast have cell walls and cell membranes of yeast. The intracellular components include amino acids, nucleic acid-related substances, minerals, and vitamins as main components.

The capsule substrates derived from yeast are produced from, for example, Torula yeast, baker's yeast, brewer's yeast, or sake yeast. The form of the capsule substrates derived from yeast is not particularly limited, and may be, for example, any of a compressed yeast form, a dry yeast form, an active dry yeast form, a killed yeast form, and a sterilized dry yeast form.

The capsule substrates derived from yeast may be a substance derived from solid components of yeast. The substance derived from solid components of yeast has a composition substantially the same as the composition of solid components of yeast. Specifically, the capsule substrates derived from yeast may be a crushed product or a powder of solid components of yeast.

The yeast used for producing capsule substrates derived from yeast is not particularly limited, and may be, for example, a yeast belonging to the genus *Saccharomyces* or a yeast belonging to the genus *Candida*. For example, the yeast may be *Saccharomyces cerevisiae*. Alternatively, the yeast may be *Candida utilis*.

Note that the first particles p1 are not limited to capsule substrates derived from yeast. The first particles p1 may be, for example, yeast, algae such as euglena, lactic acid bacteria, acetic acid bacteria, *Bacillus subtilis*, or cell membrane fragments. The yeast, euglena, lactic acid bacteria, acetic acid bacteria, and *Bacillus subtilis*, may be viable or killed. For example, the yeast, algae such as euglena, lactic acid bacteria, acetic acid bacteria, and *Bacillus subtilis* may be dried before or after sterilization. The first particles p1 are not limited to microorganisms, and may be animal cells or plant cells.

Alternatively, the first particles p1 may be vesicles. More specifically, the first particles p1 may be, for example, liposomes. A surface membrane of a vesicle is composed of lipids. More specifically, the surface membrane of the vesicle has a lipid bilayer. A liposome is a vesicle of which surface membrane consists of phospholipids. Liposomes are used as a capsule material in a drug delivery system (DDS). The capsule material used in the DDS encapsulates, for example, a physiologically active substance as an encapsulation target component pt.

<First Particle Preparation Step S1>

The first particle preparation step S1 may include a first particle production step of producing the first particles p1. When the first particles p1 are capsule substrates derived from yeast, the first particle production step S1 includes a step of releasing intracellular components from yeast. The treatment for releasing intracellular components from the yeast is not particularly limited, and may be, for example, any of a hot water treatment method, an autolysis method, and an enzymatic decomposition method.

For example, the hot water treatment method is a treatment in which a solution at a high temperature is agitated for a specified time. Yeast as a solute is added to the solution. The solvent is, for example, distilled water. However, the solvent is not limited to distilled water. The solvent may be any liquid that can cause the yeast to release the intracellular components. For example, a buffer or an emulsifier may be used as the solvent.

When releasing intracellular components from yeast by the hot water treatment method, solid components remaining after release of intracellular components from yeast may be subjected to an enzyme treatment of adding protease and/or cellulase. Further, an emulsifier may be added to the solid components. The timing of adding the emulsifier may be before or after the enzyme treatment. Alternatively, the timing of adding the emulsifier may be simultaneous with the enzyme treatment.

After release of intracellular components from yeast, remaining solid components may be sterilized. That is, the capsule substrates derived from yeast may be sterilized. In addition, in the final stage of the first particle production step, the solid components may be dried. That is, the capsule substrates derived from yeast may be in a dry state. However, the first particles p1 are not limited to those in a dry state. The first particles p1 may be in a form of a paste containing an appropriate amount of water.

<First Observation Step S2>

In the first observation step S2, first particles p1 subjected to magnetophoresis are observed. Specifically, each of the first particles p1 subjected to magnetophoresis is observed using an analyzer 10 described with reference to FIG. 2.

<First Migration Velocity Measurement Step S3>

In the first migration velocity measurement step S3, a magnetophoretic velocity v1 of each of the first particles p1 is measured based on an observation result in the first observation step S2. Specifically, a magnetophoretic velocity v1 of each of the first particles p1 is measured using the analyzer 10 described with reference to FIG. 2. In the present embodiment, the particle diameter d1 of each of the first particles p1 is measured based on the result of observation in the first observation step S2 together with the magnetophoretic velocity v1 of each of the first particles p1.

<First Magnetic Susceptibility Measurement Step S4>

In the first magnetic susceptibility measurement step S4, a volume magnetic susceptibility $\chi s1$ of each of the first particles p1 is measured based on the result of measurement in the first migration velocity measurement step S3. Specifically, a volume magnetic susceptibility $\chi s1$ of each of the first particles p1 is measured using the analyzer 10 described with reference to FIG. 2.

<Encapsulation Treatment Step S5>

In the encapsulation treatment step S5, second particles p2 are obtained by performing an encapsulation treatment so that the first particles p1 encapsulate an encapsulation target component pt smaller than the first particles p1. The second particles p2 are the first particles p1 after the encapsulation treatment. More specifically, in the encapsulation treatment step S5, the first particles p1 and the encapsulation target component pt are mixed and brought into contact with each other. Here, the first particles p1 to be subjected to the encapsulation treatment may be first particles p1 of which a volume magnetic susceptibility $\chi s1$ has been measured in advance or a first particles p1 of which a volume magnetic susceptibility $\chi s1$ has not yet been measured. The second particles p2 may be, for example, microcapsules. For example, when the first particles p1 are capsule substrates derived from yeast, the second particles p2 are microcapsules.

The encapsulation target component pt is not particularly limited and may be any component that can be encapsulated in the first particles p1. The encapsulation target component pt may be liquid or solid. The encapsulation target component pt may be, for example, a pharmaceutical, a pesticide, a flavor, or a food material.

Specifically, the encapsulation target component pt may be a physiologically active substance, a mineral, a flavor, a spice extract, a flavor oil, an animal fat, or a vegetable fat. Examples of the flavor include d-limonene, carvone, ethyl caproate, chili flavor, vanilla flavor, grill flavor, wasabi flavor, coffee flavor, pepper, black pepper, mustard, curry spice, and animal meat flavor.

Specifically, the encapsulation target component pt may be a hydrophobic substance or a hydrophilic substance. Further, the encapsulation target component pt may be a fat-soluble substance or a fat-insoluble substance. When the first particle p1 has a hydrophobic region inside thereof, a hydrophobic substance is more stably encapsulated in the first particle p1 as compared with a hydrophilic substance. Likewise, when the first particle p1 has a hydrophilic region inside thereof, a hydrophilic substance is more stably encapsulated in the first particle p1 as compared with a hydrophobic substance.

The hydrophobic substance may be, for example, at least one derived lipid selected from the group consisting of long-chain hydrocarbons, long-chain alcohols, long-chain amino alcohols, long-chain aldehydes, long-chain ketones, long-chain acids and salts thereof, terpenoids, steroids, and carotenoids. Alternatively, the hydrophobic substance may be, for example, at least one simple lipid selected from the group consisting of waxes, glycerides, ether glycerides, and ceramides. Alternatively, the hydrophobic substance may be, for example, at least one complex lipid selected from the group consisting of phospholipids, glycolipids, phosphoglycolipids, sulfolipids, and aminolipids. The hydrophilic substance may be, for example, at least one substance selected from the group consisting of amino acids, water-soluble vitamins, nucleotides, and sugars.

The encapsulation treatment is not particularly limited and may be any treatment through which encapsulation target component pt is encapsulated in the first particles p1. For example, the encapsulation treatment may be a treatment that involves mixing and agitating the first particles p1 and the encapsulation target component pt in a solvent. The solvent is, for example, distilled water. However, the solvent is not limited to distilled water. The solvent may be any liquid in which the first particles p1 and the encapsulation target component pt can be mixed and dispersed. For example, the solvent may be a buffer, a sugar solution, a salt solution, a seasoning solution, or a dashi (Japanese soup stock made from fish, kelp, or the like). When the solvent contains a salt, the amount of the encapsulation target component pt encapsulated in the first particles p1 can be increased as compared with the case where the solvent does not contain any salts.

The encapsulation treatment may include a treatment through which a dispersion obtained by mixing the first particles p1 and encapsulation target component pt in a solvent is dried. As a result of the drying, second particles p2 in a dry state are obtained. The treatment for drying the dispersion is not particularly limited and may be any treatment through which second particles p2 in a dry state can be obtained. The dispersion may be dried by spray drying, heat drying, freeze drying, or vacuum drying, for example.

The encapsulation treatment is not limited to a treatment where the first particles p1 and the encapsulation target component pt are mixed and agitated in a solvent. For example, the encapsulation treatment may be a treatment of adjusting environmental factors of a system in which the first particles p1 and the encapsulation target component pt are dispersed. Environmental factors include heat, pressure, ion concentration, pH value, and the like. For example, by adjusting ion concentration, the encapsulation target component pt can be moved into the first particles p1 due to effects of coexisting ions. Specifically, the encapsulation target component pt moves into the first particles p1 based on the second law of thermodynamics. When the first particles p1 are a viable yeast and the encapsulation target component pt is zinc (mineral), the encapsulation treatment may be a treatment that involves culturing the yeast in a medium or a culture liquid supplemented with zinc.

<Second Observation Step S6>

In the second observation step S6, second particles p2 that are the first particles after the encapsulation treatment subjected to magnetophoresis are observed. Specifically, in the same manner as in the first observation step S2, each of second particles p2 subjected to magnetophoresis is observed using an analyzer 10 described with reference to FIG. 2.

<Second Migration Velocity Measurement Step S7>

In the second migration velocity measurement step S7, a magnetophoretic velocity v2 of each of the second particles p2 is measured based on an observation result in the second observation step S6. Specifically, in the same manner as in the first migration velocity measurement step S3, a magnetophoretic velocity v2 of each of the second particles p2 is measured using the analyzer 10 described with reference to FIG. 2. In the present embodiment, the particle diameter d2 of each of the second particles p2 is measured based on the result of observation in the second observation step S6 together with the magnetophoretic velocity v2 of each of the second particles p2.

<Second Magnetic Susceptibility Measurement Step S8>

In the second magnetic susceptibility measurement step S8, a volume magnetic susceptibility $\chi s2$ of each of the second particles p2 is measured based on the result of measurement in the second migration velocity measurement step S7. Specifically, in the same manner as in the first magnetic susceptibility measurement step S4, a volume magnetic susceptibility $\chi s2$ of each of the second particles p2 is measured using the analyzer 10 described with reference to FIG. 2.

<Magnetic Susceptibility Analysis Step S9>

In the magnetic susceptibility analysis step S9, whether or not the encapsulation target component pt is encapsulated in the second particles p2 is analyzed based on a result of measurement in the first magnetic susceptibility measurement step S4 and a result of measurement in the second magnetic susceptibility measurement step S8. Specifically, whether a volume magnetic susceptibility $\chi s1$ of the first particles p1 and a volume magnetic susceptibility $\chi s2$ of the second particles p2 are the same or different is analyzed. When the volume magnetic susceptibility $\chi s1$ of the first particles p1 and the volume magnetic susceptibility $\chi s2$ of the second particles p2 are different values from each other, it is determined that the encapsulation target component pt is encapsulated in the second particles p2.

Specifically, a volume magnetic susceptibility $\chi s2$ of the second particles p2 differs depending on the component of the second particles p2. Accordingly, a volume magnetic susceptibility $\chi s2$ of the second particles p2 differs depending on whether or not the second particles p2 encapsulate the encapsulation target component pt. In other words, a volume magnetic susceptibility $\chi s2$ of the second particles p2 encapsulating the encapsulation target component pt is different from a volume magnetic susceptibility $\chi s2$ of the second particles p2 not encapsulating the encapsulation target component pt. Specifically, as a result of encapsulating the encapsulation target component pt, the second particle p2 have a volume magnetic susceptibility $\chi s2$ closer to a volume magnetic susceptibility $\chi st$ of the encapsulation target component pt as compared to a volume magnetic susceptibility $\chi s2$ of the second particle p2 not encapsulating the encapsulation target component pt.

Accordingly, by comparing a volume magnetic susceptibility $\chi s1$ of the first particles p1 and a volume magnetic susceptibility $\chi s2$ of the second particles p2, whether or not the encapsulation target component pt is encapsulated in the second particles p2 can be determined. More specifically, when a volume magnetic susceptibility $\chi s2$ of the second particles p2 is closer to a volume magnetic susceptibility $\chi st$ of the encapsulation target component pt as compared to a volume magnetic susceptibility $\chi s1$ of the first particles p1, it is determined that the encapsulation target component pt is encapsulated in the second particles p2.

After the measurement of the volume magnetic susceptibility χs2, the second particles p2 may be dried. The second particles p2 in a dry state may be obtained by drying a solution (dispersion) of the second particles p2 as a solute (dispersoid) after the second observation step S6, for example. The treatment for drying the dispersion is not particularly limited and may be any treatment through which second particles p2 in a dry state can be obtained. The dispersion may be dried by spray drying, heat drying, freeze drying, or vacuum drying, for example.

<Analyzer 10>

Figure 2:
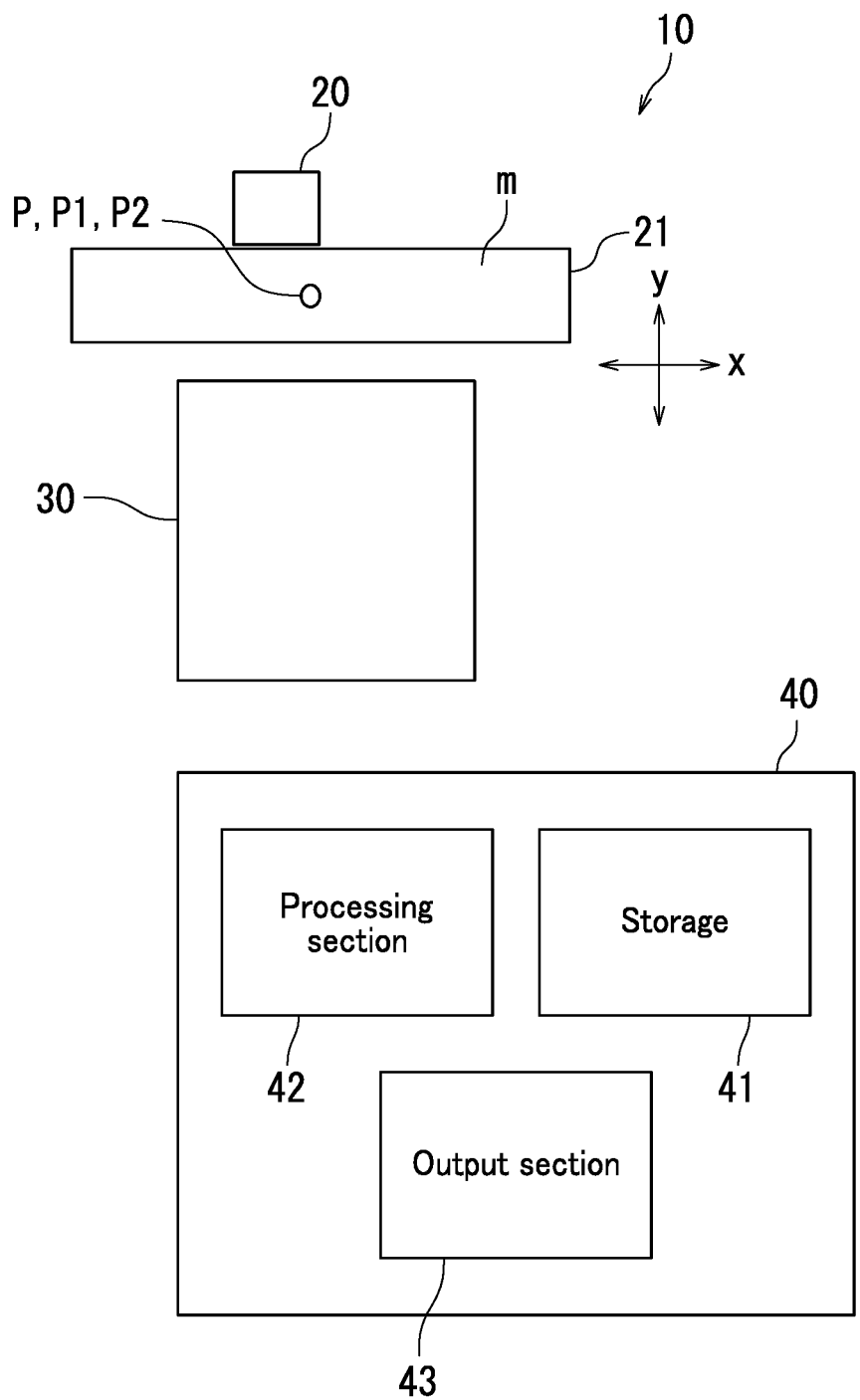
FIG. 2 is a schematic diagram of an analyzer of the first embodiment of the present disclosure.

Next, with reference to FIGS. 1 and 2, an analyzer 10 of the present embodiment will be described. FIG. 2 is a schematic diagram of the analyzer 10 of the present embodiment. The analyzer 10 analyzes whether or not the encapsulation target component pt is encapsulated in the second particles p2.

As illustrated in FIG. 2, the analyzer 10 includes a magnetic field generator 20, an observing section 30, and a calculating section 40. In a vicinity of the magnetic field generator 20, a cell 21 is disposed. The magnetic field generator 20 generates a magnetic field to subject the particles p in the cell 21 to magnetophoresis. The observing section 30 observes the particles p in the cell 21. The calculating section 40 measures a particle diameter d and a magnetophoretic velocity v of each of the particles p based on the result of observation by the observing section 30. Furthermore, the calculating section 40 measures a volume magnetic susceptibility χs based on the particle diameter d and the magnetophoretic velocity v of each of the particles p.

Specifically, in the first observation step S2, the magnetic field generator 20 subjects the first particles p1 in the cell 21 to magnetophoresis and the observing section 30 observes the first particles p1 in the cell 21. In the first migration velocity measurement step S3, the calculating section 40 measures a magnetophoretic velocity v1 of each of the first particles p1 based on the result of observation by the observing section 30. In the present embodiment, the calculating section 40 measures a particle diameter d1 of each of the first particles p1 together with the magnetophoretic velocity v1 of each of the first particles p1 based on the result of observation by the observing section 30. Furthermore, in the first magnetic susceptibility measurement step S4, the calculating section 40 measures a volume magnetic susceptibility χs1 based on the magnetophoretic velocity v1 and the particle diameter d1 of each of the first particles p1.

Furthermore, in the second observation step S6, the magnetic field generator 20 subjects the second particles p2 in the cell 21 to magnetophoresis and the observing section 30 observes the second particles p2 in the cell 21. In the second migration velocity measurement step S7, the calculating section 40 measures a magnetophoretic velocity v2 of each of the second particles p2 based on the result of observation by the observing section 30. In the present embodiment, the calculating section 40 measures a particle diameter d2 of each of the second particles p2 together with the magnetophoretic velocity v2 of each of the second particles p2 based on the result of observation by the observing section 30. Furthermore, in the second magnetic susceptibility measurement step S8, the calculating section 40 measures a volume magnetic susceptibility χs2 based on the magnetophoretic velocity v2 and the particle diameter d2 of each of the second particles p1.

Furthermore, in the magnetic susceptibility analysis step S9, the calculating section 40 analyzes whether or not the encapsulation target component pt is encapsulated in the second particles p2 based on the volume magnetic susceptibility χs1 of the first particles p1 and the volume magnetic susceptibility χs2 of the second particles p2.

The following describes the analyzer 10 in further detail. The magnetic field generator 20 generates a magnetic field gradient (a gradient of magnetic flux density) and causes a magnetic force to act on the particles p in the cell 21. As a result, the particles p migrate through magnetophoresis. In the present embodiment, the magnetic field generator 20 includes two permanent magnets 20a and 20b (see FIGS. 3A and 3B) that generate a magnetic field gradient. The two permanent magnets 20a and 20b are arranged at a specific distance of, for example, at least 100 μm and no greater than 500 μm from each other with a gap therebetween. The cell 21 is disposed in the gap between the two permanent magnets 20a and 20b.

In the present embodiment, the cell 21 is a capillary tube. A capillary tube is an example of a tubular member. The material of the cell 21 is not particularly limited and may be any material through which visible light or laser light can transmit. The cell 21 is made of glass or plastic, for example.

The particles p are introduced into the cell 21 together with a medium m using, for example, a microsyringe, a micropump, or an autosampler. Alternatively, the particles p can be introduced into the cell 21 together with a medium m based on the siphon principle. Alternatively, a droplet containing the particles p may be introduced into the cell 21 (capillary tube) by capillary action. When a droplet containing the particles p is dropped on one end of the capillary tube, the droplet flows through the capillary tube by capillary action.

The particles p are present in the medium m. The medium m may contain only one particle p or a plurality of particles p therein. When a plurality of particles p are present in the medium m, the plurality of particles p may be dispersed in the medium m or unevenly distributed in the medium m. The medium m is, for example, distilled water. The analyzer 10 measures respective volume magnetic susceptibilities χs of the plurality of particles p in the medium m.

The observing section 30 observes the particles p in the cell 21 and generates signals indicating observation results. The calculating section 40 measures a magnetophoretic velocity v and a particle diameter d of each of the particles p based on the signals generated by the observing section 30. The calculating section 40 includes a storage 41, a processing section 42, and an output section 43.

The storage 41 stores a program, setting information, and the like. The storage 41 is configured by a storage device and semiconductor memory, for example. The storage device is a hard disk drive (HDD), for example. The storage 41 includes random access memory (RAM) and read only memory (ROM) as semiconductor memory, for example.

The processing section 42 performs various processes such as numerical calculation, information processing, and device control by executing a program stored in the storage 41. For example, the processing section 42 is configured by a processor such as a central processing unit (CPU) or a microcomputer. Alternatively, the processing section 42 may be configured by an integrated circuit such as an application specific integrated circuit (ASIC). The integrated circuit has a logic circuit. The processing section 42 may be configured by a processor and an integrated circuit. Note that a general-purpose computer such as a personal computer, for example, may be used as the calculating section 40.

The processing section 42 measures temporal change in the position of a particle p in the cell 21 based on observation results of the observing section 30 (signals generated by the observing section 30). For example, the processing section 42 measures the position of a particle p in the cell 21 at specified time intervals. In other words, the position of the particle p is measured at different times. The processing section 42 measures a magnetophoretic velocity v of the particle p based on temporal change in the position of the particle p.

In addition, the processing section 42 measures the particle diameter d of the particle p based on the signals generated by the observing section 30. Furthermore, the processing section 42 measures a volume magnetic susceptibility $\chi s$ based on the magnetophoretic velocity v and the particle diameter d of the particle p.

For example, the processing section 42 calculates the volume magnetic susceptibility $\chi s$ of the particle p based on the following formula (1).

$$v = \{2(\chi s - \chi m) r^2 / 9 \eta \mu_o\} B (dB/dx) \quad (1)$$

In the formula (1), v is a magnetophoretic velocity of a particle p, $\chi s$ is a volume magnetic susceptibility of the particle p, $\chi m$ is a volume magnetic susceptibility of the medium m, r is a radius of the particle p, $\eta$ is a viscosity of a medium m, to is a magnetic permeability under vacuum, B is a magnetic flux density, and dB/dx is a magnetic field gradient (flux density gradient). The formula (1) is derived from the fact that the difference between the magnetic force applied to the particle p and the medium m in the axial direction (x direction) of the cell 21 (capillary tube) is substantially equal to the viscous resistance force.

Note that the magnetophoretic velocity v and the volume magnetic susceptibility $\chi s$ are values measured by the processing section 42. The radius r of the particle p is calculated by the processing section 42 from a measured particle diameter d of the particle p, for example. The volume magnetic susceptibility $\chi m$ of the medium m, the viscosity $\eta$ of the medium m, the magnetic permeability to under vacuum, the magnetic flux density B, and the magnetic field gradient dB/dx are stored in the storage 41 in advance. For example, an analyst can store a volume magnetic susceptibility $\chi m$ of the medium m, a viscosity $\eta$ of the medium m, a magnetic permeability to under vacuum, a magnetic flux density B, and a magnetic field gradient dB/dx in the storage 41 by operating an input device such as a keyboard, a mouse, or a touch display. The volume magnetic susceptibility $\chi m$ of the medium m, the viscosity $\eta$ of the medium m, and the magnetic permeability to under vacuum are values found in literature, for example. The magnetic flux density B and the magnetic field gradient dB/dx are measured values, for example.

The storage 41 stores a volume magnetic susceptibility $\chi s1$ of the first particles p1 measured in the first magnetic susceptibility measurement step S4. Furthermore, the storage 41 stores a volume magnetic susceptibility $\chi s2$ of the second particles p2 measured in the second magnetic susceptibility measurement step S8. The processing section 42 accesses the storage 41 to acquire the volume magnetic susceptibility $\chi s1$ of the first particles p1 and the volume magnetic susceptibility $\chi s2$ of the second particles p2 from the storage 41. Thereafter, the processing section 42 analyzes whether or not the encapsulation target component pt is encapsulated in the second particles p2 by comparing the volume magnetic susceptibility $\chi s1$ of the first particles p1 and the volume magnetic susceptibility $\chi s2$ of the second particles p2. More specifically, when a volume magnetic susceptibility $\chi s2$ of the second particles p2 is closer to a volume magnetic susceptibility $\chi st$ of the encapsulation target component pt as compared to a volume magnetic susceptibility $\chi s1$ of the first particles p1, the processing section 42 determines that the encapsulation target component pt is encapsulated in the second particles p2.

Note that the volume magnetic susceptibility $\chi st$ of the encapsulation target component pt is stored in the storage 41 in advance. The volume magnetic susceptibility $\chi st$ of the encapsulation target component pt is a value found in literature, for example. In this case, the analyst stores the volume magnetic susceptibility $\chi st$ (literature value) of the encapsulation target component pt in the storage 41 by operating an input device. Alternatively, the analyst may measure the volume magnetic susceptibility $\chi st$ of the encapsulation target component pt using the analyzer 10. In this case, a volume magnetic susceptibility $\chi st$ of the encapsulation target component pt measured by the processing section 42 is stored in the storage 41.

The output section 43 outputs an analysis result (determination result) by the processing section 42. Specifically, the output section 43 outputs information indicating whether or not the encapsulation target component pt is encapsulated in the second particles p2. The output section 43 includes, for example, a display. In this case, the processing section 42 displays information indicating the analysis result on the display. The output section 43 may include a communication interface in addition to or instead of the display. The communication interface is, for example, a universal serial bus (USB) connector. In this case, the processing section 42 outputs a signal indicating the analysis result to an external device via the communication interface and a USB cable. The external device is, for example, a display or a printer. When the external device is a display, information indicating the analysis result is displayed on the external device. When the external device is a printer, an image indicating the analysis result is printed out. Alternatively, the external device may be a USB memory. In this case, the processing section 42 outputs a signal indicating the analysis result to the USB memory via the communication interface. As a result, information indicating the analysis result is stored in the USB memory.

Figure 3A:
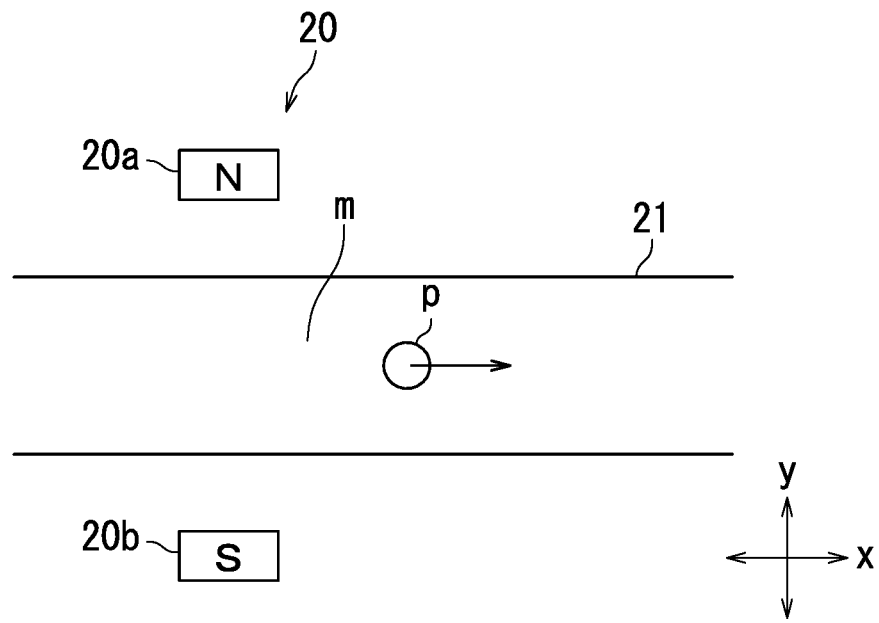
FIGS. 3A and 3B are each a diagram illustrating movement of a particle.
Figure 3B:
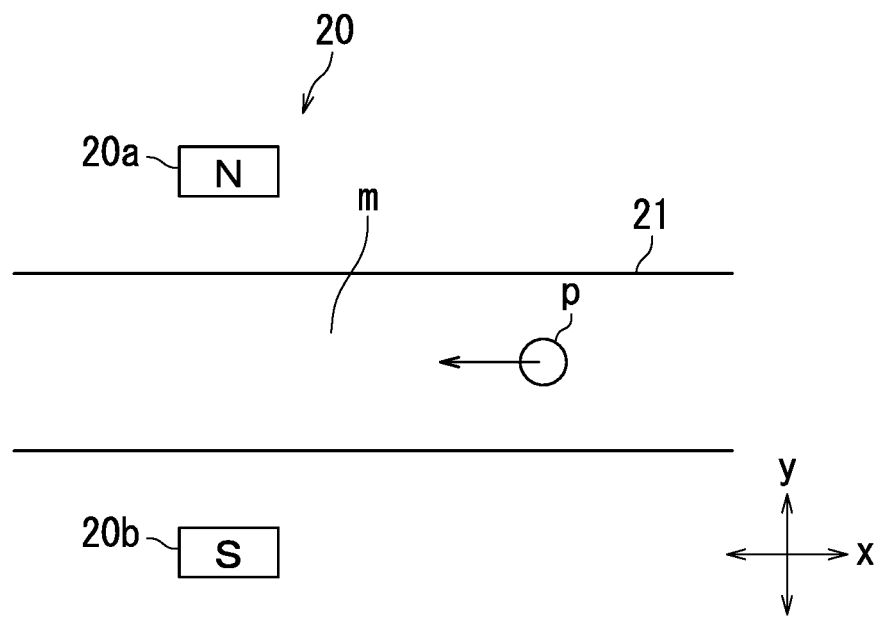

Next, with reference to FIGS. 3A and 3B, movement of a particle p will be described. FIGS. 3A and 3B are each a diagram illustrating movement of a particle p. As illustrated in FIGS. 3A and 3B, the magnetic field generator 20 includes a permanent magnet 20a having an N magnetic pole and a permanent magnet 20b having an S magnetic pole. The two permanent magnets 20a and 20b oppose each other having the cell 21 therebetween.

When the volume magnetic susceptibility $\chi s$ of the particle p is lower than the volume magnetic susceptibility $\chi m$ of the medium m, the particle p moves in a direction away from the magnetic field (magnetic field generator 20) as illustrated in FIG. 3A. By contrast, when the volume magnetic susceptibility $\chi s$ of the particle p is higher than the volume magnetic susceptibility $\chi m$ of the medium m, the particle p moves in a direction toward the magnetic field (magnetic field generator 20) as illustrated in FIG. 3B.

As illustrated in FIGS. 3A and 3B, the movement of a particle p is determined according to the relation between the volume magnetic susceptibility $\chi s$ of the particle p and the volume magnetic susceptibility $\chi m$ of the medium m. Note that the particle p receives a force in the vicinity of an end of each of the permanent magnets 20a and 20b. For example, the particle p receives a force within a range of ±200 μm from the end of each of the permanent magnets 20a and 20b.

Figure 4:
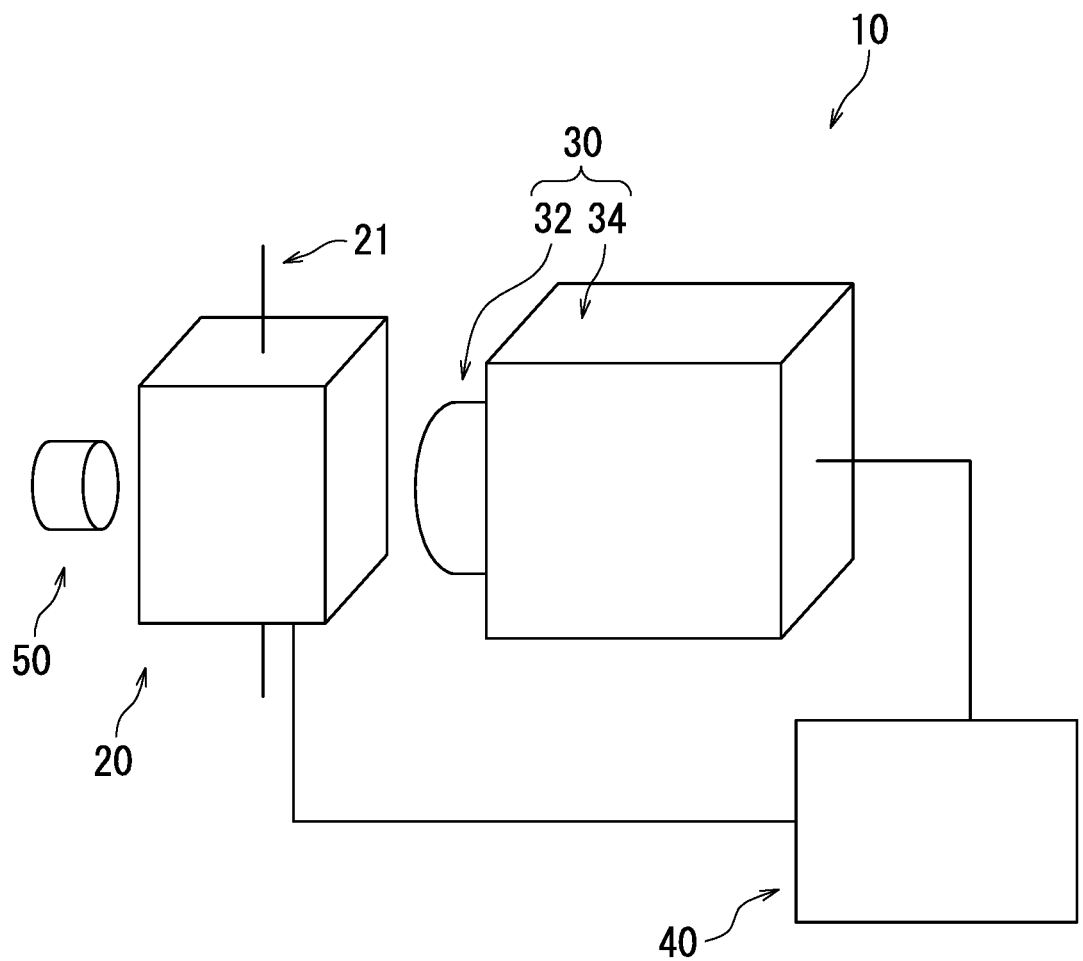
FIG. 4 is a diagram illustrating a configuration of an analyzer according to the first embodiment of the present disclosure.

Next, with reference to FIG. 4, the analyzer 10 will be further described. FIG. 4 is a diagram illustrating a configuration of the analyzer 10. As illustrated in FIG. 4, the analyzer 10 further includes a light source 50. The observing section 30 includes an enlarging section 32 and an imaging section 34.

The light source 50 emits light that has a relatively high intensity and includes visible light components. The light source 50 irradiates the cell 21 with light. As a result, the particle p is irradiated with light. The wavelength spectrum of the light emitted from the light source 50 may be relatively broad. As the light source 50, a halogen lamp is preferably used, for example.

The particle p introduced into the cell 21 is enlarged at an appropriate magnification by the enlarging section 32 and imaged by the imaging section 34. The position of the particle p can be determined based on an imaging result of the imaging section 34 (an image captured by the imaging section 34). For example, the enlarging section 32 includes an objective lens, and the imaging section 34 includes a charge coupled device (CCD). Alternatively, each pixel of the imaging section 34 may be configured by a photodiode or a photomultiplier. The imaging section 34 images the particle p at specified time intervals, for example. Note that the imaging section 34 may image light emitted from the light source 50 and transmitted through the cell 21 or image light emitted from the light source 50 and scattered by the particle p.

The calculating section 40 (the processing section 42) measures temporal change in the position of the particle p based on imaging results of the imaging section 34, and measures a magnetophoretic velocity v of the particle p based on the temporal change in the position of the particle p.

In addition, the calculating section 40 (the processing section 42) measures the particle diameter d of the particle p based on an imaging result of the particle p. For example, the calculating section 40 (the processing section 42) performs the following process. First, an image captured by the imaging section 34 is converted into a monochrome image, and the luminance is quantified. Next, the boundary of the particle p is set by comparing a differential value of the luminance value with a threshold value. Next, the area of the particle p is detected based on the boundary set as above, and the particle diameter d is calculated from the radius of a circle corresponding to the area. Alternatively, the center of the particle p is defined, a plurality of straight lines passing through the center of the particle p are drawn, the distance between two points at which the straight line intersects the boundary of the particle p is determined for each of the straight lines, and an average of the distances is calculated.

The first embodiment of the present disclosure has been described so far with reference to FIGS. 1 to 4. According to the present embodiment, whether or not the encapsulation target component pt is encapsulated in the analysis target particles (the second particles p2) can be analyzed for each analysis target.

The particles p to be measured for the volume magnetic susceptibility $\chi s1$ may be all or part of the first particles p1 prepared in the first particle preparation step S1. Likewise, the particles p to be measured for the volume magnetic susceptibility $\chi s2$ may be all or part of the second particles p2 obtained in the encapsulation treatment step S5.

Second Embodiment

Next, with reference to FIG. 5, a second embodiment of the present disclosure will be described. Here, matters different from the first embodiment will be described, and description of the same matters as those in the first embodiment will be omitted. The second embodiment differs from the first embodiment in that the second particles p2 are analyzed spectroscopically.

Figure 5:
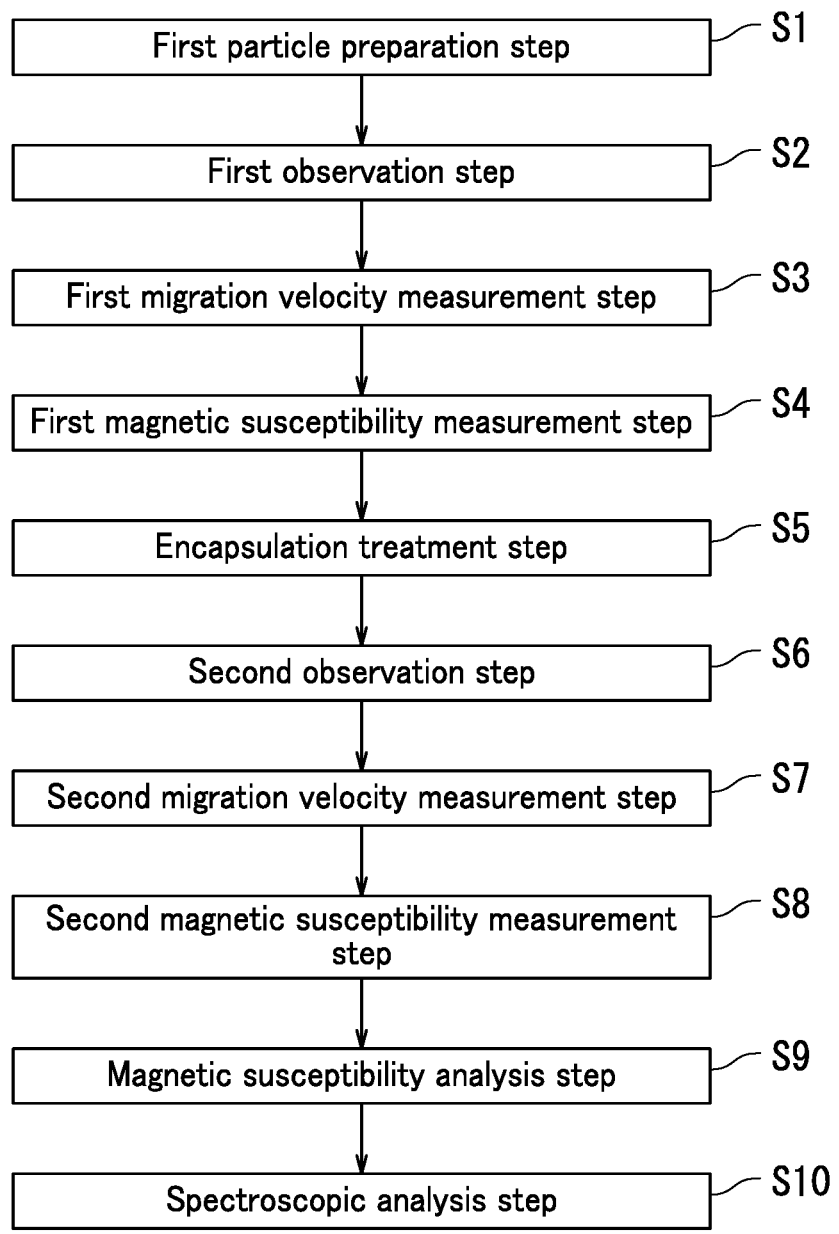
FIG. 5 is a flowchart illustrating a method for particle production according to a second embodiment of the present disclosure.

FIG. 5 is a flowchart illustrating a method for particle production according to the present embodiment. The method for particle production according to the present embodiment further includes a spectroscopic analysis step S10.

<Spectroscopic Analysis Step S10>

In the spectroscopic analysis step S10, the second particles p2 are spectroscopically observed to analyze whether or not the encapsulation target component pt is encapsulated in the second particles p2. Specifically, the second particles p2 are irradiated with laser light, scattered light from the second particles p2 is detected, and a spectrum of the scattered light is analyzed. By analyzing the spectrum of the scattered light from a specimen, the molecular structure of the specimen can be identified. Accordingly, based on scattered light from the second particles p2, whether or not the encapsulation target component pt is encapsulated in the second particles p2 can be analyzed. Specifically, whether or not a spectrum indicating the encapsulation target component pt is included in the spectrum of the scattered light is analyzed.

By analyzing the Raman spectrum using a Raman spectrometer for example, whether or not the encapsulation target component pt is encapsulated in the second particles p2 can be analyzed. The Raman spectrometer may include a microscope. In other words, the Raman spectrometer may be a confocal Raman microscope.

Specifically, the Raman spectrometer includes a laser light source, a detector, and a calculator. The laser light source irradiates the second particles p2 with laser light to generate scattered light from the second particles p2. The detector detects the scattered light. The calculator of the Raman spectrometer analyzes the spectrum of the scattered light based on the output of the detector. Specifically, the calculator identifies the molecular structure of the second particles p2 by analyzing the spectrum of the scattered light. The calculator includes, for example, a microcomputer or an ASIC.

Note that the calculating section 40 described with reference to FIG. 2 may be used for analyzing the spectrum of the scattered light. Specifically, the output from the detector of the Raman spectrometer is input to the calculating section 40. The processing section 42 of the calculating section 40 analyzes the spectrum of the scattered light based on the output of the detector, and based on the analysis result, analyzes whether or not a spectrum indicating the encapsulation target component pt is included in the spectrum of the scattered light.

The second embodiment of the present disclosure has been described so far with reference to FIG. 5. According to the present embodiment, in addition to the analysis based on the volume magnetic susceptibility $\chi s1$ of the first particles p1 and the volume magnetic susceptibility $\chi s2$ of the second particles p2, spectroscopic analysis on whether or not the encapsulation target component pt is encapsulated in the second particles p2 can be achieved. Therefore, whether or not the encapsulation target component pt is encapsulated in the analysis target particles (the second particles p2) can be analyzed for each analysis target in a further reliable manner.

The particles p to be spectroscopically analyzed may be all or part of the second particles p2 obtained in the encapsulation treatment step S5.

In the flowchart in FIG. 5, the spectroscopic analysis step S10 is performed following the magnetic susceptibility analysis step S9. However, the order of performance of the spectroscopic analysis step S10 is not necessarily immediately after the magnetic susceptibility analysis step S9. The spectroscopic analysis step S10 may be performed before the second observation step S6, for example.

Although a Raman spectrometer was used in the present embodiment, the spectrometer is not limited to the Raman spectrometer. For example, an ultraviolet-visible spectrometer or an infrared spectrometer may be used. When an ultraviolet-visible spectrometer is used, whether or not the encapsulation target component pt is encapsulated in the second particles p2 is analyzed by analysis of an ultraviolet-visible absorption spectrum. When an infrared spectrometer is used, whether or not the encapsulation target component pt is encapsulated in the second particles p2 is analyzed by analysis of an infrared spectrum. Alternatively, whether or not the encapsulation target component pt is encapsulated in the second particles p2 may be analyzed by acquisition of a near-infrared spectrum using an infrared spectrometer and subsequent analysis of the near-infrared spectrum through statistical processing. In other words, chemometrical analysis of a near-infrared spectrum may be used to analyze whether or not the encapsulation target component pt is encapsulated in the second particles p2.

Third Embodiment

Next, with reference to FIG. 6, a third embodiment of the present disclosure will be described. Here, matters different from the first and second embodiments will be described, and description of the same matters as those in the first and second embodiments will be omitted. The third embodiment differs from the first and second embodiments in that the zeta potentials of the first particles p1 and the second particles p2 are analyzed.

Figure 6:
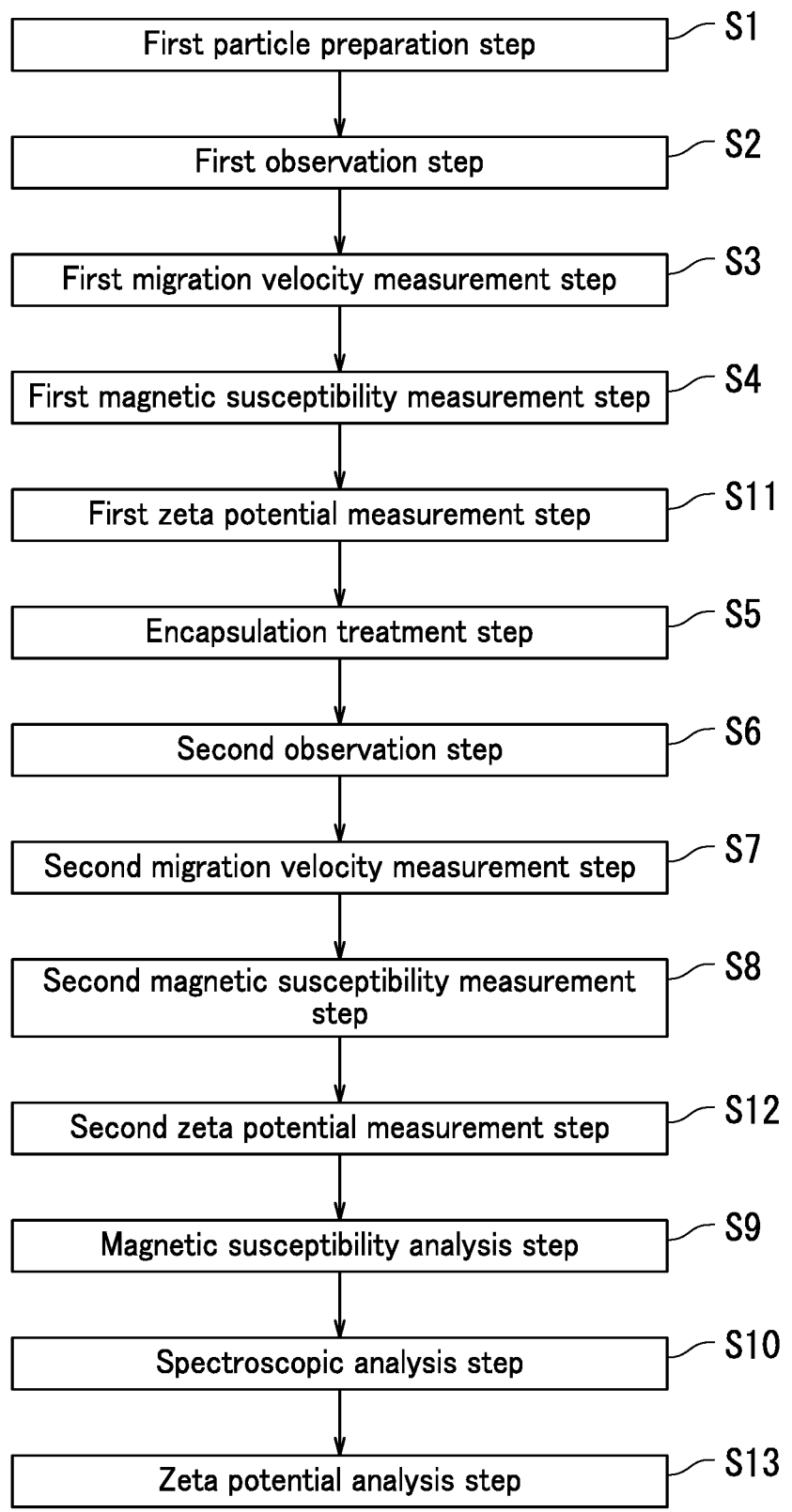
FIG. 6 is a flowchart illustrating a method for particle production according to a third embodiment of the present disclosure.

FIG. 6 is a flowchart illustrating a method for particle production according to the present embodiment. The method for particle production according to the present embodiment further includes a first zeta potential measurement step S11, a second zeta potential measurement step S12, and a zeta potential analysis step S13.

<First Zeta Potential Measurement Step S11>

In the first zeta potential measurement step, a zeta potential of the first particles p1 is measured. Specifically, the first particles p1 are electrophoresed in a medium m, and the electrophoretic velocity of the first particles p1 is measured. Based on the electrophoretic velocity, a zeta potential of the first particles p1 is measured.

Specifically, the zeta potential is measured using a zeta potential measurement device. The zeta potential measurement device includes a positive electrode and a negative electrode. A cell is disposed between the positive electrode and the negative electrode. A solution in which the first particles p1 as a solute (dispersoid) are dispersed is sealed in the cell. The zeta potential measurement device applies a voltage to the positive electrode to generate an electric field between the positive electrode and the negative electrode. As a result, the first particles p1 are electrophoresed. Zeta potential measurement devices are of two types: a device for measuring an average zeta potential value of all the particles p dispersed in the cell and a device for measuring individual zeta potential values of all the particles p dispersed in the cell.

The device for measuring an average zeta potential value further includes a laser light source, a detector, and a calculator. The laser light source irradiates the first particles p1 as a whole subjected to electrophoresis with laser light to generate scattered light from the first particles p1 as a whole. The detector detects the scattered light. Specifically, the frequency of the scattered light generated from the first particles p1 as a whole subjected to electrophoresis shifts (changes) due to the Doppler effect. The detector detects the frequency of the scattered light shifted (changed) by the Doppler effect.

The calculator of the device for measuring an average zeta potential value measures an average electrophoretic velocity value based on the output of the detector. Specifically, the amount of shift (amount of change) in the frequency of the scattered light is proportional to the average electrophoretic velocity value. The calculator measures the average electrophoretic velocity value of the first particles p1 as a whole by measuring the amount of shift in the frequency of the scattered light. The calculator subsequently measures the average zeta potential value based on the average electrophoretic velocity value. The calculator includes, for example, a microcomputer or an ASIC. As the calculator, the calculating section 40 described with reference to FIG. 2 may be used.

As with the device for measuring an average zeta potential value, the device for measuring individual zeta potential values of the particles p further includes a laser light source, a detector, and a calculator. The laser light source irradiates the first particles p1 as a whole subjected to electrophoresis with laser light to generate scattered light from the first particles p1 as a whole. The detector includes an objective lens and an image sensor. The image sensor may be a semiconductor sensor such as a CCD image sensor or a CMOS image sensor. The detector captures an image of the light enlarged by the objective lens using an image sensor. As a result, how each of the first particles p1 moves is imaged.

The calculator of the device for measuring individual zeta potential values of the particles p measures individual electrophoretic velocities of the first particles p1 based on the imaging signals output from the detector. The calculator subsequently measures the zeta potential of each of first particles p1 based on the individual electrophoretic velocities. The calculator includes, for example, a microcomputer or an ASIC. As the calculator, the calculating section 40 described with reference to FIG. 2 may be used.

<Second Zeta Potential Measurement Step S12>

In the second zeta potential measurement step, a zeta potential of the second particles p2 is measured. The second zeta potential measurement step S12 is the same as the first zeta potential measurement step S11 in all aspects other than that the measurement target is the second particles p2.

<Zeta Potential Analysis Step S13>

In the zeta potential analysis step S13, whether or not the encapsulation target component pt is encapsulated in the second particles p2 is analyzed based on a result of measurement in the first zeta potential measurement step S11 and a result of measurement in the second zeta potential measurement step S12. Specifically, by comparing a zeta potential of the first particles p1 and a zeta potential of the second particles p2, whether the zeta potential of the first particles p1 and the zeta potential of the second particles p2 are the same or different is analyzed. When the zeta potential of the first particles p1 and the zeta potential of the second particles p2 are of the same value, it is determined that the encapsulation target component pt is encapsulated in the second particles p2.

Specifically, when the encapsulation target component pt is attached to the surfaces of the second particles p2 without entering the inside of the second particles p2, the zeta potential of the second particles p2 is a different value from the value of the zeta potential of the first particles p1. In other words, when the encapsulation target component pt enters the inside of the second particles p2 without being attached to the surfaces of the second particles p2, the zeta potential of the second particles p2 and the zeta potential of the first particles p1 are of the same value. Accordingly, whether or not the encapsulation target component pt is encapsulated in the second particles p2 can be analyzed by comparing a zeta potential of the first particles p1 and a zeta potential of the second particles p2.

Note that the calculating section 40 described with reference to FIG. 2 may be used for the analysis of the zeta potentials of the first particles p1 and the second particles p2. Specifically, the analyst stores data indicating a zeta potential of the first particles p1 and data indicating a zeta potential of the second particles p2 in the storage 41 by operating an input device. Alternatively, the analyst connects the zeta potential measurement device and the calculating section 40 via a transmission cable such as a USB cable, for example, to transmit data indicating a zeta potential of the first particles p1 and data indicating a zeta potential of the second particles p2 from the zeta potential measurement device to the calculating section 40. The processing section 42 of the calculating section 40 analyzes whether or not the encapsulation target component pt is encapsulated in the second particles p2 by comparing the zeta potential of the first particles p1 and the zeta potential of the second particles p2.

The third embodiment of the present disclosure has been described so far with reference to FIG. 6. According to the present embodiment, whether or not the encapsulation target component pt is encapsulated in the second particles p2 can be analyzed based on the zeta potentials of the first particles p1 and the second particles p2, in addition to the analysis based on the volume magnetic susceptibility χs1 of the first particles p1 and the volume magnetic susceptibility χs2 of the second particles p2 and the spectroscopic analysis. Accordingly, whether or not the encapsulation target component pt is encapsulated in the analysis target particles (the second particles p2) can be analyzed for each analysis target in a further reliable manner.

The particles p to be measured for the zeta potential in the first zeta potential measurement step S11 may be all or part of the first particles p1 prepared in the first particle preparation step S1. Likewise, the particles p to be measured for the zeta potential in the second zeta potential measurement step S12 may be all or part of the second particles p2 obtained in the encapsulation treatment step S5.

In the flowchart in FIG. 6, the first zeta potential measurement step S11 is performed following the first magnetic susceptibility measurement step S4. However, the order of performance of the first zeta potential measurement step S11 is not necessarily immediately after the first magnetic susceptibility measurement step S4. The first zeta potential measurement step S11 may be performed before the first observation step S2, for example.

Similarly, in the flowchart in FIG. 6, the second zeta potential measurement step S12 is performed following the second magnetic susceptibility measurement step S8. However, the order of performance of the second zeta potential measurement step S12 is not necessarily immediately after the second magnetic susceptibility measurement step S8.

The second zeta potential measurement step S12 may be performed before the second observation step S6, for example.

Furthermore, in the flowchart in FIG. 6, the zeta potential analysis step S13 is performed following the spectroscopic analysis step S10. However, the order of performance of the zeta potential analysis step S13 is not necessarily immediately after the spectroscopic analysis step S10. The zeta potential analysis step S13 is only required to be performed after the second zeta potential measurement step S12. The zeta potential analysis step S13 may be performed before the magnetic susceptibility analysis step S9, for example.

Furthermore, in the present embodiment, the spectroscopic analysis step S10 is performed, but the spectroscopic analysis step S10 may be omitted.

The embodiments of the present disclosure have been described so far with reference to the drawings. The present disclosure is not limited to the above embodiments, and can be implemented in various manners within a scope not departing from the gist thereof.

For example, in the embodiments according to the present disclosure, the particle diameter d of the particle p is measured by image analysis, but the particle diameter d of the particle p may be measured by analyzing the Brownian motion of the particle p.

Specifically, a diffusion coefficient can be calculated from variance of positional change (displacement) of the particle p in a direction (y direction) perpendicular to the axial direction (x direction) of the cell 21 (capillary tube), and then the particle diameter d of the particle p can be calculated from the diffusion coefficient. More specifically, the particle p is influenced by the magnetic field gradient in the axial direction (x direction) of the cell 21 (capillary tube), but is hardly influenced by the magnetic field gradient in the direction (y direction) perpendicular to the axial direction of the cell 21. Accordingly, a diffusion coefficient D can be calculated from the variance of positional displacement of the particle p in the y direction. Specifically, the diffusion coefficient D can be calculated by dividing the square of the moving distance of the particle p performing the Brownian motion in the y direction by twice the time.

The processing section 42 determines the particle diameter d of the particle p from the diffusion coefficient D based on the following formula (2). In the formula (2), d is a particle diameter of the particle p, k is the Boltzmann constant, T is an absolute temperature, and η is a viscosity of the medium m.

$$d = kT/(3\zeta\eta D) \quad (2)$$

In the embodiments of the present disclosure, the analyzer 10 includes the light source 50. However, the analyzer 10 may include a laser light source instead of the light source 50, or include a laser light source in addition to the light source 50. In the cases where the analyzer 10 includes the light source 50 and a laser light source, when light is emitted from the light source 50, the emission of laser light from the laser light source is stopped. Likewise, when laser light is emitted from the laser light source, the emission of light from the light source 50 is stopped. In the cases where a laser light source is used, the particles p introduced into the cell 21 are irradiated with laser light. The observing section 30 observes the particles p by means of the laser light (scattered light) scattered by the particles p in the cell 21. For example, the imaging section 34 described with reference to FIG. 4 images the laser light scattered by the particles p via the enlarging section 32.

In the cases where a laser light source is used, the particle diameter d of the particle p may be measured by, for example, a dynamic light scattering method or a static light scattering method. In the cases where the particles p are irradiated with laser light, the capillary tube is preferably a square capillary having a square cross section perpendicular to the axial direction. Mirror finishing of a side surface to be irradiated with laser light is easier when the capillary used as the cell 21 is a square capillary.

In the embodiments of the present disclosure, the calculating section 40 (processing section 42) measured the particle diameter d of the particle p. However, the analyst may measure the particle diameter d of the particle p based on an image that has been imaged by the imaging section 34 and displayed on a display. Alternatively, the analyst may measure the particle diameter d of the particle p based on an image that has been imaged by the imaging section 34 and then printed out. In this case, the analyst stores data indicating a particle diameter d in the storage 41 by operating an input device.

In the embodiments of the present disclosure, the particle diameter d was measured. However, a literature value may be used as the particle diameter d. In this case, the analyst stores data indicating a particle diameter d in the storage 41 by operating an input device.

In the embodiments of the present disclosure, a magnetophoretic velocity v of the particle p was measured by the imaging section 34 imaging the particle p at specified time intervals. However, the magnetophoretic velocity v of the particle p may be measured based on, for example, the laser Doppler method.

EXAMPLES

The following describes the present disclosure more specifically with reference to examples. However, the present disclosure is not limited to the scope of the examples.

Example 1

<Production of Yeast-Derived Capsule Substrate>

First, yeast-derived capsule substrates D11 were produced. The yeast-derived capsule substrates may be referred to below as "yeast capsule substrates". In Example 1, soluble components were removed from baker's yeast by the hot water treatment method to give solid components in a paste form, and the solid components were sterilized and dried to give yeast capsule substrates D11. The yeast capsule substrates D11 were in a dry state. Thereafter, the yeast capsule substrates D11 were made into a paste form. Specifically, the yeast capsule substrates D11 in a dry state were added to distilled water to prepare a solution L1, and the solution L1 was heated for sterilization. Thereafter, the solution L1 was cooled to room temperature so that the yeast capsule substrates D11 might be made into a paste form.

<Washing Treatment>

Washing treatment was performed twice. Specifically, the yeast capsule substrates D11 in the paste form were added to distilled water, followed by agitation to prepare a solution L2. Thereafter, centrifugation was performed to separate off distilled water from the solution L2, and thus yeast capsule substrates D11 after a first washing treatment were obtained. The yeast capsule substrates D11 after the first washing treatment were added to distilled water again, followed by agitation to prepare a solution L3. Thereafter, centrifugation was performed to separate off distilled water from the solution L3, and thus yeast capsule substrates D11 after a second washing treatment were obtained. The "yeast capsule substrates D11 after the second washing treatment" and the like may be referred to below as "yeast capsule substrates D11 after washing" and the like. Note that the yeast capsule substrates D11 after washing were in a paste form.

<Volume Magnetic Susceptibility Measurement for a Capsule Substrate Derived from Yeast>

The volume magnetic susceptibility of a first specimen SP1 (the yeast capsule substrates D11 after washing) was individually measured. Specifically, a first specimen SP1 (the yeast capsule substrates D11 after washing) was added to distilled water, and then the distilled water was irradiated with ultrasonic waves (ultrasonic treatment) to prepare a solution L4. After the ultrasonic treatment, the solution L4 was sealed in a cell, and the volume magnetic susceptibility of the first specimen SP1 (the yeast capsule substrates D11 after washing) was individually measured. After the measurement of the volume magnetic susceptibility, the solution L4 was sealed in a hemocytometer, and particles of the first specimen SP1 (the yeast capsule substrates D11 after washing) were counted using a microscope.

<Encapsulation Treatment>

An encapsulation treatment was performed using the yeast capsule substrates D11 in the paste form, d-limonene, and distilled water. The mixing ratio of the yeast capsule substrates D11 in the paste form, d-limonene, and distilled water was 2:1:7 by weight. Here, the ratio of mixed d-limonene is the weight of d-limonene given that the weight of the yeast capsule substrates D11 is "2". Likewise, the ratio of mixed distilled water is the weight of distilled water given that the weight of the yeast capsule substrates D11 is "2".

Specifically, d-limonene was added to distilled water, and then the temperature of the distilled water was raised. Thereafter, the yeast capsule substrates D11 in the paste form were added to the distilled water, followed by agitation to prepare a solution L5. After the agitation, the solution L5 was heated for sterilization. Thereafter, the solution L5 was cooled to room temperature to prepare microcapsules D12 in a paste form. The microcapsules D12 are the yeast capsule substrates D11 after being subjected to the encapsulation treatment. Note that d-limonene is a hydrophobic substance, and the yeast capsule substrates D11 each have a hydrophobic region inside thereof.

<Washing Treatment>

Washing treatment was performed twice. Specifically, the microcapsules D12 in the paste form were added to distilled water, followed by agitation to prepare a solution L6. Thereafter, centrifugation was performed to separate off distilled water from the solution L6, and thus microcapsules D12 after a first washing treatment were obtained. The microcapsules D12 after the first washing treatment were added to distilled water again, followed by agitation to prepare a solution L7. Thereafter, centrifugation was performed to separate off distilled water from the solution L7, and thus microcapsules D12 after a second washing treatment were prepared. The "microcapsules D12 after the second washing treatment" and the like may be referred to below as "microcapsules D12 after washing" and the like. Note that the microcapsules D12 after washing were in a paste form.

<Volume Magnetic Susceptibility Measurement for Microcapsules>

The volume magnetic susceptibility of a second specimen SP2 (the microcapsules D12 after washing) was individually measured. Specifically, a second specimen SP2 was added to distilled water, and then the distilled water was irradiated with ultrasonic waves (ultrasonic treatment) to prepare a solution L8. After the ultrasonic treatment, the solution L8 was sealed in a cell, and the volume magnetic susceptibility of the second specimen SP2 (the microcapsules D12 after washing) was individually measured. After the measurement of the volume magnetic susceptibility, the solution L8 was sealed in a hemocytometer, and particles of the second specimen SP2 (the microcapsules D12 after washing) were counted using a microscope.

Table 1 shows the measurement results of Example 1.

TABLE 1

|  | Average particle diameter [μm] | Average volume magnetic susceptibility/$10^{-6}$ |
|---|---|---|
| Before encapsulation treatment (D11) | 5.12 | −9.46 |
| After encapsulation treatment (D12) | 6.08 | −9.23 |
| Difference | −0.96 | −0.23 |

Figure 7:
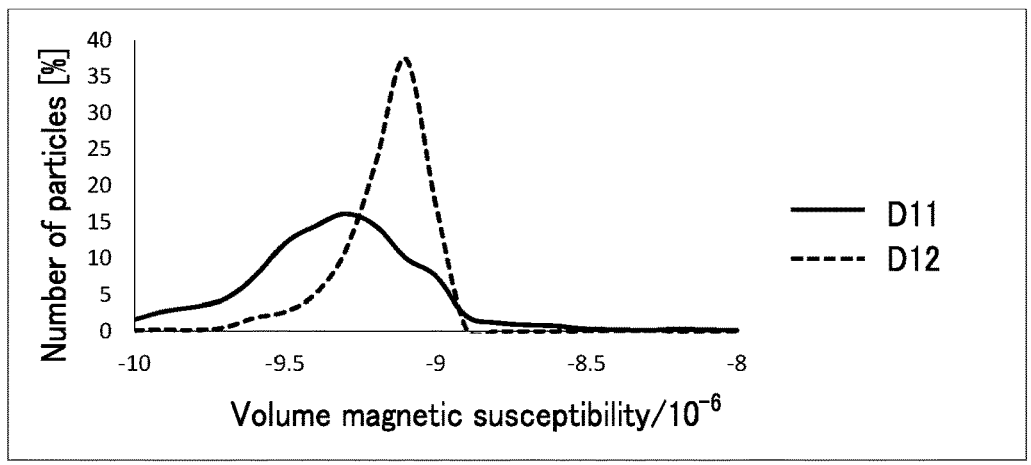
FIG. 7 is a diagram illustrating measurement results of Example 1.

FIG. 7 is a diagram illustrating measurement results of Example 1. Specifically, FIG. 7 illustrates measurement results of volume magnetic susceptibility for the first specimen SP1 (the yeast capsule substrates D11 after washing) and the second specimen SP2 (the microcapsules D12 after washing). The first specimen SP1 and the second specimen SP2 correspond to the first particles p1 and the second particles p2 of the above-described embodiments, respectively. In FIG. 7, the horizontal axis represents volume magnetic susceptibility, and the vertical axis represents percentage (%) of number of particles. In FIG. 7, the solid line graph represents measurement results of volume magnetic susceptibility for the first specimen SP1 (the yeast capsule substrates D11 after washing), and the broken line graph represents measurement results of volume magnetic susceptibility for the second specimen SP2 (the microcapsules D12 after washing).

Specifically, the solid line graph was created by measuring individual volume magnetic susceptibilities of the particles of the first specimen SP1 and calculating the percentage of the number of the particles of the first specimen SP1 at each volume magnetic susceptibility. Similarly, the broken line graph was created by measuring individual volume magnetic susceptibilities of the particles of the second specimen SP2 and calculating the percentage of the number of the particles of the second specimen SP2 at each volume magnetic susceptibility.

As shown in Table 1 and FIG. 7, the first specimen SP1 and the second specimen SP2 have different volume magnetic susceptibilities. The reason for the difference in the volume magnetic susceptibility is that d-limonene is encapsulated in the microcapsules D12. Specifically, the volume magnetic susceptibility of d-limonene is "−8.48×$10^{-6}$". As shown in Table 1, the average value of the volume magnetic susceptibilities of the second specimen SP2 (the microcapsules D12 after washing) is closer to the volume magnetic susceptibility of d-limonene as compared to the average value of the volume magnetic susceptibilities of the first specimen SP1 (the yeast capsule substrates D11 after washing). In addition, as shown in FIG. 7, the peak in the volume magnetic susceptibility of the second specimen SP2 (the microcapsules D12 after washing) is closer to the volume magnetic susceptibility of d-limonene as compared to the peak in the volume magnetic susceptibility of the first specimen SP1 (the yeast capsule substrates D11 after washing). Thus, encapsulation of d-limonene in the microcapsules D12 was quantitatively analyzed.

Example 2

In Example 2, the volume magnetic susceptibilities of a first specimen SP11 (yeast capsule substrates D21 after washing) and the volume magnetic susceptibilities of a second specimen SP12 (microcapsules D22 after washing) were measured in the same manner as in Example 1. Example 2 is the same as Example 1 in all aspects other than that the type of yeast capsule substrates is different. Specifically, in Example 2, after solid components in a paste form were obtained from baker's yeast by the hot water treatment method, an emulsifier was added to the solid components in the paste form. Thereafter, a protease was further added to the solid components in the paste form. Glycerin fatty acid ester was used as the emulsifier. An endoprotease was used as the protease. Note that the yeast capsule substrates D21 each have a hydrophobic region inside thereof.

Table 2 shows the measurement results of Example 2.

TABLE 2

|  | Average particle diameter [μm] | Average volume magnetic susceptibility/$10^{-6}$ |
|---|---|---|
| Before encapsulation treatment (D21) | 4.73 | −9.27 |
| After encapsulation treatment (D22) | 5.32 | −9.17 |
| Difference | −0.60 | −0.10 |

Figure 8:
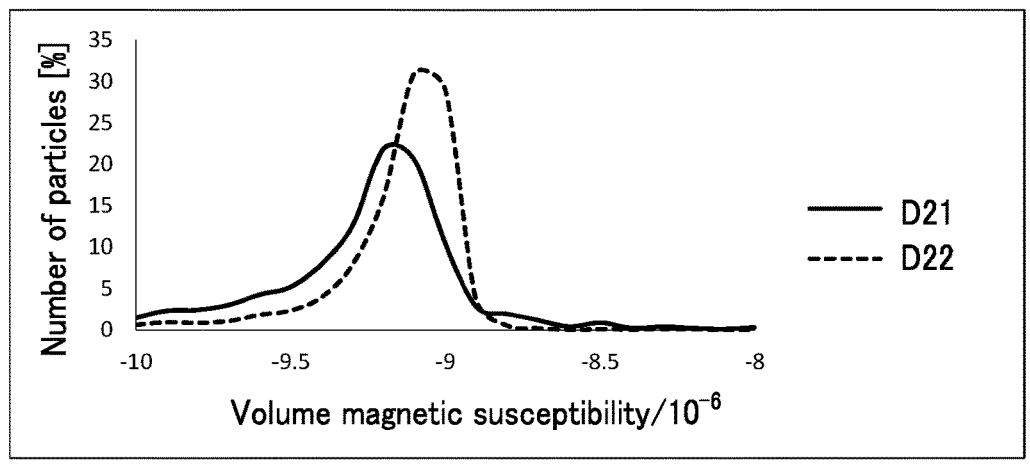
FIG. 8 is a diagram illustrating measurement results of Example 2.

FIG. 8 is a diagram illustrating measurement results of Example 2. Specifically, FIG. 8 illustrates measurement results of volume magnetic susceptibility for the first specimen SP11 and the second specimen SP12. In FIG. 8, the horizontal axis represents volume magnetic susceptibility, and the vertical axis represents percentage (%) of number of particles. In FIG. 8, the solid line graph represents measurement results of volume magnetic susceptibility for the first specimen SP11 (the yeast capsule substrates D21 after washing), and the broken line graph represents measurement results of volume magnetic susceptibility for the second specimen SP12 (the microcapsules D22 after washing).

As shown in Table 2 and FIG. 8, the first specimen SP11 and the second specimen SP12 have different volume magnetic susceptibilities. Specifically, as shown in Table 2, the average value of the volume magnetic susceptibilities of the second specimen SP12 (the microcapsules D22 after washing) is closer to the volume magnetic susceptibility of d-limonene as compared to the average value of the volume magnetic susceptibilities of the first specimen SP11 (the yeast capsule substrates D21 after washing). In addition, as shown in FIG. 8, the peak in the volume magnetic susceptibility of the second specimen SP12 (the microcapsules D22 after washing) is closer to the volume magnetic susceptibility of d-limonene as compared to the peak in the volume magnetic susceptibility of the first specimen SP11 (the yeast capsule substrates D21 after washing). Thus, encapsulation of d-limonene in the microcapsules D22 was quantitatively analyzed.

Example 3

In Example 3, the volume magnetic susceptibilities of a first specimen SP21 (yeast capsule substrates D31 after washing) and the volume magnetic susceptibilities of a second specimen SP22 (microcapsules D32 after washing) were measured in the same manner as in Example 1. Example 3 is the same as Example 1 in all aspects other than that the type of yeast and the treatment for releasing intracellular components from the yeast are different. Specifically, in Example 3, Torula yeast was used. An enzymatic decomposition method was employed to release intracellular components from the Torula yeast. Note that the yeast capsule substrates D31 each have a hydrophobic region inside thereof.

Table 3 shows the measurement results of Example 3.

TABLE 3

|  | Average particle diameter [μm] | Average volume magnetic susceptibility/$10^{-6}$ |
|---|---|---|
| Before encapsulation treatment (D31) | 4.18 | −9.27 |
| After encapsulation treatment (D32) | 4.54 | −8.97 |
| Difference | −0.36 | −0.31 |

Figure 9:
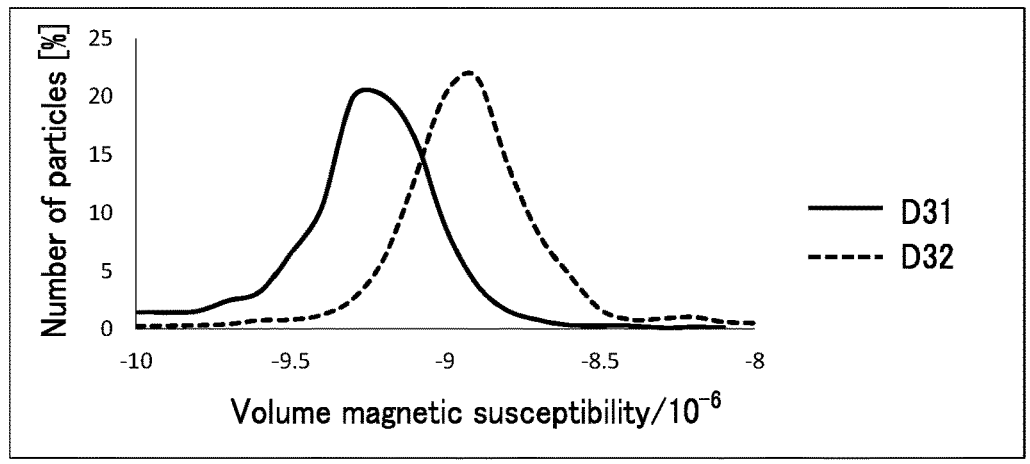
FIG. 9 is a diagram illustrating measurement results of Example 3.

FIG. 9 is a diagram illustrating measurement results of Example 3. Specifically, FIG. 9 illustrates measurement results of volume magnetic susceptibility for the first specimen SP21 and the second specimen SP22. In FIG. 9, the horizontal axis represents volume magnetic susceptibility, and the vertical axis represents percentage (%) of number of particles. In FIG. 9, the solid line graph represents measurement results of volume magnetic susceptibility for the first specimen SP21 (the yeast capsule substrates D31 after washing), and the broken line graph represents measurement results of volume magnetic susceptibility for the second specimen SP22 (the microcapsules D32 after washing).

As shown in Table 3 and FIG. 9, the first specimen SP21 and the second specimen SP22 have different volume magnetic susceptibilities. Specifically, as shown in Table 3, the average value of the volume magnetic susceptibilities of the second specimen SP22 (the microcapsules D32 after washing) is closer to the volume magnetic susceptibility of d-limonene as compared to the average value of the volume magnetic susceptibilities of the first specimen SP21 (the yeast capsule substrates D31 after washing). In addition, as shown in FIG. 9, the peak in the volume magnetic susceptibility of the second specimen SP22 (the microcapsules D32 after washing) is closer to the volume magnetic susceptibility of d-limonene as compared to the peak in the volume magnetic susceptibility of the first specimen SP21 (the yeast capsule substrates D31 after washing). Thus, encapsulation of d-limonene in the microcapsules D32 was quantitatively analyzed.

Example 4

In Example 4, the mixing ratio of the yeast capsule substrates D21 in the paste form, d-limonene, and distilled water was varied in the encapsulation treatment, and the volume magnetic susceptibility of the microcapsules D22 after washing (specimen SP3) was measured for each mixing ratio. Specifically, the mixing ratio of the yeast capsule substrates D21 in the paste form, d-limonene, and distilled water was varied in a range from "2:0:8" to "2:2.8:5.2" by weight. Specifically, the mixing ratios of the yeast capsule substrates D21, d-limonene, and distilled water were "2:0: 8", "2:0.125:7.875", "2:0.25:7.75", "2:0.5:7.5", "2:1:7", "2:2:6", "2:2.5:5.5", and "2:2.8:5.2" by weight.

Figure 10:
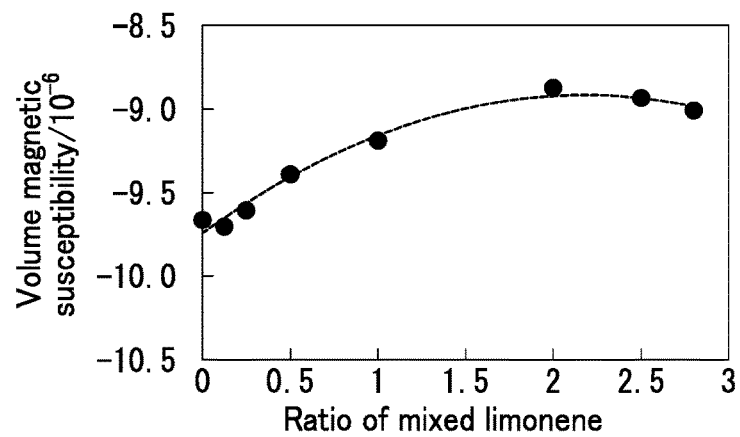
FIG. 10 is a diagram illustrating first measurement results of Example 4.

FIG. 10 is a diagram illustrating first measurement results of Example 4. Specifically, FIG. 10 illustrates measurement results of the volume magnetic susceptibility of the specimen SP3 (the microcapsules D22 after washing). In FIG. 10, the horizontal axis represents ratio (weight ratio) of mixed d-limonene, and the vertical axis represents volume magnetic susceptibility (average value).

As illustrated in FIG. 10, as the ratio of mixed d-limonene increased, the volume magnetic susceptibility of the specimen SP3 (the microcapsules D22 after washing) approached the volume magnetic susceptibility of d-limonene. The results suggest that as the ratio of the mixed encapsulation component pt increased, the encapsulation target component pt encapsulated in the microcapsules increased, changing the volume magnetic susceptibility of the microcapsules.

In Example 4, the amount of d-limonene contained in the specimen SP3 (the microcapsules D22 after washing) was further measured using a high performance liquid chromatograph (HPLC). Specifically, the specimen SP3 was added to ethanol, followed by agitation using a vortex mixer for 30 minutes to prepare a solution L9. After the agitation, the solution L9 was centrifuged. Thereafter, the supernatant was measured using a high performance liquid chromatograph (HPLC). The HPLC conditions were as follows.

Figure 11:
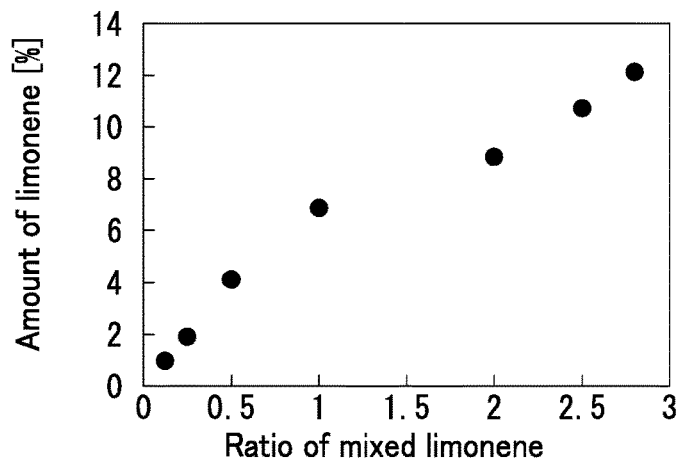
FIG. 11 is a diagram illustrating second measurement results of Example 4.

<HPLC Conditions>
High performance liquid chromatograph: product of Hitachi High-Technologies Corporation
Column: Poroshell 120 EC-C18, product of Agilent Technologies, Inc. (particle diameter: 2.7 μm, dimensions: 4.6 mm×100 mm)
Column temperature: 40° C.
Eluent: mixture of acetonitrile and water (mixing ratio of acetonitrile and water was 50:50% by weight)
Flow rate: 1 mL/min
Detector: UV light with a wavelength of 210 nm
Injection volume: 10 μL FIG. 11 is a diagram illustrating second measurement results of Example 4. Specifically, FIG. 11 illustrates measurement results of the amount of d-limonene contained in the specimen SP3. In FIG. 11, the horizontal axis represents ratio (weight ratio) of mixed d-limonene, and the vertical axis represents amount of d-limonene contained in the specimen SP3. Specifically, the vertical axis represents percentage of amount of d-limonene per gram of microcapsules.

As illustrated in FIG. 11, as the ratio of mixed d-limonene increased, the amount of d-limonene contained in the specimen SP3 (the microcapsules D22 after washing) increased. That is, by increasing the ratio of mixed d-limonene, it was possible to increase the amount of d-limonene encapsulated in the microcapsules as a result of the encapsulation treatment.

Figure 12:
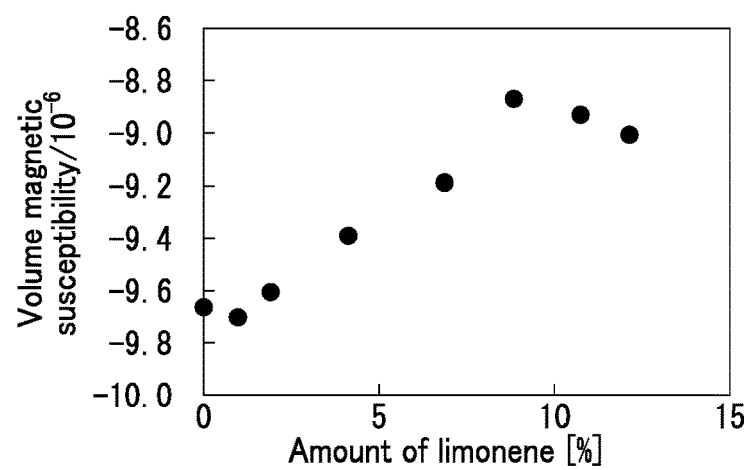
FIG. 12 is a diagram illustrating third measurement results of Example 4.

FIG. 12 is a diagram illustrating third measurement results of Example 4. Specifically, FIG. 12 illustrates a relation between the amount of d-limonene contained in the specimen SP3 and the volume magnetic susceptibility of the specimen SP3. In FIG. 12, the horizontal axis represents amount of d-limonene contained in the specimen SP3. Specifically, the horizontal axis represents percentage of amount of d-limonene per gram (unit weight) of microcapsules. The vertical axis represents volume magnetic susceptibility (average value).

As illustrated in FIG. 12, in a range where the percentage of the amount of d-limonene per unit weight was no greater than 9%, the volume magnetic susceptibility of the specimen SP3 approached the volume magnetic susceptibility of d-limonene as the amount of d-limonene per unit weight increased. By contrast, in a range where the percentage of the amount of d-limonene per unit weight was more than 9%, the volume magnetic susceptibility of the specimen SP3 decreased as the amount of d-limonene per unit weight increased. In other words, the volume magnetic susceptibility was saturated. The results confirmed that the amount of d-limonene encapsulated in the microcapsules could be quantitatively analyzed using the volume magnetic susceptibility until the volume magnetic susceptibility was saturated. The amount of d-limonene encapsulated in the microcapsules will be referred to below as "amount of encapsulated limonene".

Figure 13:
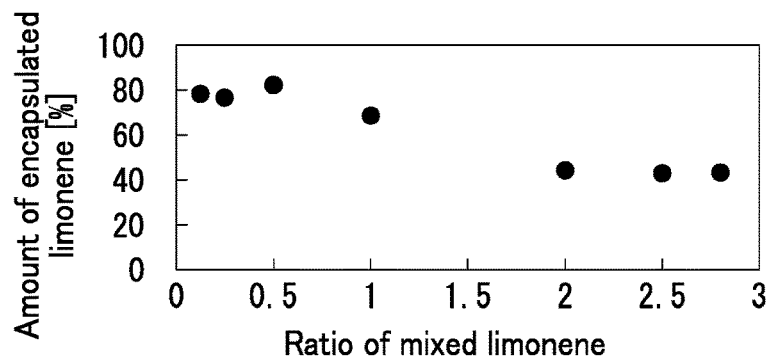
FIG. 13 is a diagram illustrating fourth measurement results of Example 4.

FIG. 13 is a diagram illustrating fourth measurement results of Example 4. Specifically, FIG. 13 illustrates the relation between the ratio of mixed d-limonene and the percentage of the amount of encapsulated limonene relative to the total amount of d-limonene used in the encapsulation treatment. The percentage of the amount of encapsulated limonene relative to the total amount of d-limonene used in the encapsulation treatment will be referred to below as "percentage of amount of encapsulated limonene". In FIG. 13, the horizontal axis represents ratio (weight ratio) of mixed d-limonene, and the vertical axis represents percentage (%) of amount of encapsulated limonene.

As illustrated in FIG. 13, as the ratio of mixed d-limonene increased, the amount of d-limonene contained in the specimen SP3 (the microcapsules D22 after washing) increased. On the other hand, as the ratio of mixed d-limonene increased, the percentage of amount of encapsulated limonene decreased. The results suggest that as the ratio of the mixed encapsulation target component pt increased, the amount of encapsulation target component pt not encapsulated in the microcapsules increased. In addition, even when the ratio of mixed d-limonene was the ratio at which all the d-limonene should be theoretically encapsulated in the microcapsules D22, the percentage of amount of encapsulated limonene did not reach 100%. The results suggest that the treatment through which encapsulation target component pt is encapsulated in microcapsules follows the theory of chemical equilibrium.

Example 5

In Example 5, sodium chloride was added to distilled water for the encapsulation treatment, and the volume magnetic susceptibility of the microcapsules D22 after washing (specimen SP4) was measured. In other words, the encapsulation treatment was performed using a sodium chloride solution as a solvent. The mixing ratio of the yeast capsule substrates D21 in a paste form, d-limonene, distilled water, and sodium chloride was 2:1:7:1 by weight.

Figure 14:
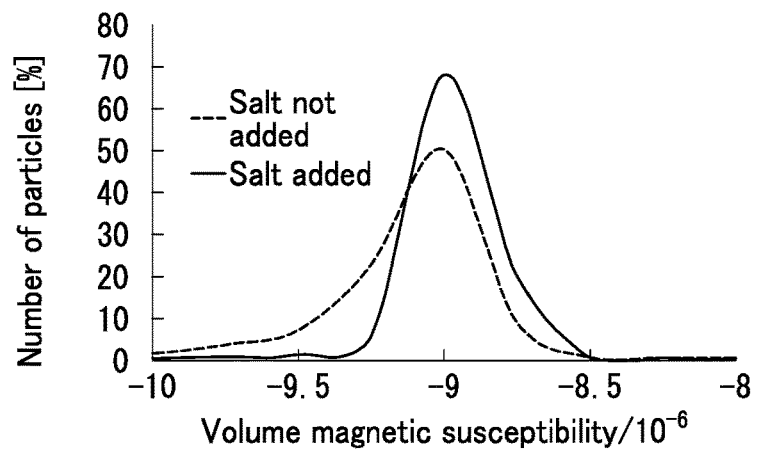
FIG. 14 is a diagram illustrating first measurement results of Example 5.

FIG. 14 is a diagram illustrating first measurement results of Example 5. Specifically, FIG. 14 illustrates measurement results of volume magnetic susceptibility for the specimen SP4. In FIG. 14, the horizontal axis represents volume magnetic susceptibility, and the vertical axis represents percentage (%) of number of particles. In FIG. 14, the solid line graph represents measurement results of volume magnetic susceptibility for the specimen SP4. In FIG. 14, measurement results for the second specimen SP12 (the microcapsules D22 after washing) described in Example 2 are also represented by the broken line graph, as a reference example.

As illustrated in FIG. 14, the volume magnetic susceptibility for the microcapsules D22 after washing came closer to the volume magnetic susceptibility of d-limonene as a result of addition of the salt.

In Example 5, the amount of d-limonene contained in the specimen SP4 (the amount of d-limonene per gram of microcapsules) was measured using a high performance liquid chromatograph in the same manner as in Example 4.

Figure 15:
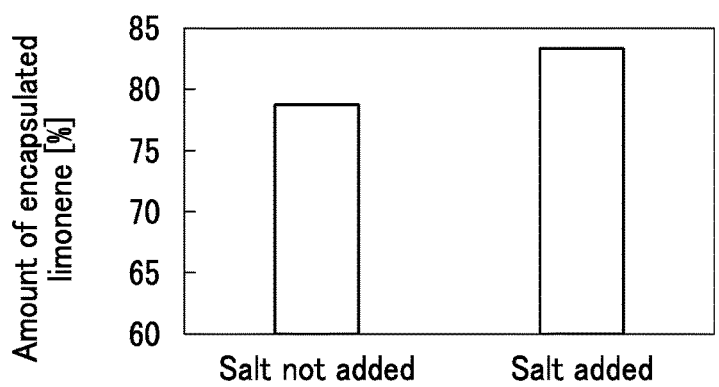
FIG. 15 is a diagram illustrating second measurement results of Example 5.

FIG. 15 is a diagram illustrating second measurement results of Example 5. Specifically, FIG. 15 illustrates the percentage of the amount of encapsulated limonene for the specimen SP4. FIG. 15 also illustrates the percentage of the amount of encapsulated limonene for the second specimen SP12 (the microcapsules D22 after washing) described in Example 2 as a reference example.

As illustrated in FIG. 15, the amount of limonene encapsulated in the microcapsules D22 after washing increased as a result of addition of the salt. That is, by adding a salt to the solvent to reduce the solubility of d-limonene in the solvent, the amount of encapsulation target component to be encapsulated in the microcapsules D22 after washing increased. The results suggest that the amount of encapsulation target component encapsulated in microcapsules depends on the solubility of the encapsulation target component in the solvent.

Example 6

In Example 6, ethyl hexanoate as an encapsulation target component was encapsulated in the yeast capsule substrates D21 to prepare a specimen SP5 (microcapsules D22 after washing), and volume magnetic susceptibility for the specimen SP5 was measured. Furthermore, in Example 6, the encapsulation treatment was performed varying the mixing ratio of the yeast capsule substrates D21 in a paste form, ethyl hexanoate, and distilled water in a range from "2:0:8" to "2:2:6" by weight. Specifically, the mixing ratios of the yeast capsule substrates D21, ethyl hexanoate, and distilled water were "2:0:8", "2:0.125:7.875", "2:0.25:7.75", "2:0.5: 7.5", "2:1:7", and "2:2:6" by weight. Here, the ratio of mixed ethyl hexanoate and the ratio of mixed distilled water are the weight of ethyl hexanoate and the weight of distilled water, respectively given that the weight of the yeast capsule substrates D21 is "2". Note that ethyl hexanoate is a hydrophobic substance.

Figure 16:
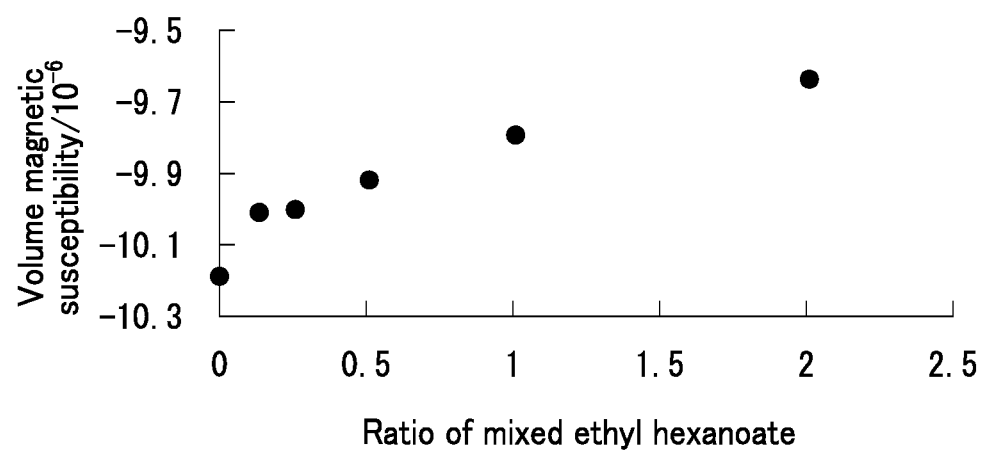
FIG. 16 is a diagram illustrating measurement results of Example 6.

FIG. 16 is a diagram illustrating measurement results of Example 6. Specifically, FIG. 16 illustrates measurement results of volume magnetic susceptibility for the specimen SP5. In FIG. 16, the horizontal axis represents ratio (weight ratio) of mixed ethyl hexanoate, and the vertical axis represents volume magnetic susceptibility (average value).

As illustrated in FIG. 16, as the ratio of mixed ethyl hexanoate increased, the volume magnetic susceptibility of the specimen SP5 (the microcapsules D22 after washing) approached the volume magnetic susceptibility of ethyl hexanoate. The volume magnetic susceptibility of ethyl hexanoate is $-6.94 \times 10^{-6}$. The results suggest that as the ratio of the mixed encapsulation target component increased, the encapsulation target component encapsulated in the microcapsules increased, changing the volume magnetic susceptibility of the microcapsules.

What is claimed is:
1. A method for particle analysis, the method comprising:
  a first observation step of observing first particles subjected to magnetophoresis;
  a first migration velocity measurement step of measuring a magnetophoretic velocity of the first particles based on an observation result in the first observation step;
  a first magnetic susceptibility measurement step of measuring a volume magnetic susceptibility of each of the first particles based on a result of measurement in the first migration velocity measurement step;

an encapsulation treatment step of performing an encapsulation treatment so that the first particles encapsulate an encapsulation target component smaller than the first particles;

a second observation step of observing second particles that are the first particles after the encapsulation treatment subjected to magnetophoresis;

a second migration velocity measurement step of measuring a magnetophoretic velocity of the second particles based on an observation result in the second observation step;

a second magnetic susceptibility measurement step of measuring a volume magnetic susceptibility of each of the second particles based on a result of measurement in the second migration velocity measurement step;

a step of analyzing whether or not the encapsulation target component is encapsulated in the second particles based on a result of measurement in the first magnetic susceptibility measurement step and a result of measurement in the second magnetic susceptibility measurement step;

a first zeta potential measurement step of measuring a zeta potential of the first particles;

a second zeta potential measurement step of measuring a zeta potential of the second particles; and a step of analyzing whether or not the encapsulation target component is encapsulated in the second particles based on a result of measurement in the first zeta potential measurement step and a result of measurement in the second zeta potential measurement step.

2. The method for particle analysis according to claim 1, further comprising a step of spectroscopically observing the second particles to analyze whether or not the encapsulation target component is encapsulated in the second particles.

3. A method for particle production, the method comprising:

a first observation step of observing first particles subjected to magnetophoresis;

a first migration velocity measurement step of measuring a magnetophoretic velocity of the first particles based on an observation result in the first observation step;

a first magnetic susceptibility measurement step of measuring a volume magnetic susceptibility of each of the first particles based on a result of measurement in the first migration velocity measurement step;

an encapsulation treatment step of performing an encapsulation treatment so that the first particles encapsulate an encapsulation target component smaller than the first particles;

a second observation step of observing second particles that are the first particles after the encapsulation treatment subjected to magnetophoresis;

a second migration velocity measurement step of measuring a magnetophoretic velocity of the second particles based on an observation result in the second observation step;

a second magnetic susceptibility measurement step of measuring a volume magnetic susceptibility of each of the second particles based on a result of measurement in the second migration velocity measurement step;

a step of analyzing whether or not the encapsulation target component is encapsulated in the second particles based on a result of measurement in the first magnetic susceptibility measurement step and a result of measurement in the second magnetic susceptibility measurement step;

a first zeta potential measurement step of measuring a zeta potential of the first particles;

a second zeta potential measurement step of measuring a zeta potential of the second particles; and a step of analyzing whether or not the encapsulation target component is encapsulated in the second particles based on a result of measurement in the first zeta potential measurement step and a result of measurement in the second zeta potential measurement step.

4. The method for particle production according to claim 3, wherein the first particles include solid components of yeast remaining after release of intracellular components from the yeast.

5. The method for particle production according to claim 4, further comprising a first particle production step of producing the first particles, wherein the first particle production step comprises a step of causing the yeast to release the intracellular components.

6. The method for particle production according to claim 3, wherein the encapsulation treatment step includes a step of mixing the first particles and the encapsulation target component in a solvent.

* * * * *